(12) United States Patent
Yoshino et al.

(10) Patent No.: US 9,181,254 B2
(45) Date of Patent: Nov. 10, 2015

(54) METHOD FOR PRODUCING SEPIAPTERIN AND TETRAHYDROLACTOYLPTERIN

(71) Applicant: SHIRATORI PHARMACEUTICAL CO., LTD., Narashino-shi (JP)

(72) Inventors: Hiroshi Yoshino, Narashino (JP); Taichi Komoda, Narashino (JP); Yuichi Shiro, Chiba (JP); Shunichi Murata, Narashino (JP); Shizuaki Murata, Mie-gun (JP); Yasuhiro Kuroda, Yokkaichi (JP)

(73) Assignee: SHIRATORI PHARMACEUTICAL CO., LTD., Narashino-shi (JP)

( * ) Notice: Subject to any disclaimer, the term of this patent is extended or adjusted under 35 U.S.C. 154(b) by 0 days.

(21) Appl. No.: 14/398,884

(22) PCT Filed: May 7, 2013

(86) PCT No.: PCT/JP2013/062817
§ 371 (c)(1),
(2) Date: Nov. 4, 2014

(87) PCT Pub. No.: WO2013/168693
PCT Pub. Date: Nov. 14, 2013

(65) Prior Publication Data
US 2015/0119574 A1      Apr. 30, 2015

(30) Foreign Application Priority Data

May 7, 2012    (JP) .................................. 2012-105758
Nov. 9, 2012   (JP) .................................. 2012-247255

(51) Int. Cl.
*C07D 475/00*      (2006.01)
*C07D 475/04*      (2006.01)

(52) U.S. Cl.
CPC .................................. *C07D 475/04* (2013.01)

(58) Field of Classification Search
None
See application file for complete search history.

(56) References Cited

U.S. PATENT DOCUMENTS

| 4,713,454 A | 12/1987 | Sakai et al. |
| 2007/0244322 A1 | 10/2007 | Moser et al. |
| 2013/0197000 A1 | 8/2013 | Hasegawa et al. |

FOREIGN PATENT DOCUMENTS

| JP | 61-172877 | 8/1986 |
| WO | WO 2005/049614 A2 | 6/2005 |
| WO | WO 2011/132435 A1 | 10/2011 |

OTHER PUBLICATIONS

International Search Report issued Aug. 13, 2013, in PCT/JP13/062817 filed May 7, 2013.
Written Opinion of the International Searching Authority issued Aug. 13, 2013, in PCT/JP13/062817 filed May 7, 2013.
Fan, et al., "Partial Purification and Some Properties of Biopterin Synthase and Dihydropterin Oxidase from *Drosophila melanogaster*", Biochemical Genetics, vol. 17, No. 3-4, 1979, 20 pages.
Landge, et al., "Chemoselective oxidation of 6-hydroxyalkylpteridine and its application to synthesis of 6-acyl-7,8-dihydropteridine", Heterocycles, vol. 71, No. 4, 2007, pp. 911-918.
Choi, et al., "Functional role of sepiapterin reductase in the biosynthesis of tetrahydropteridines in *Dictyostelium discoideum* Ax2", Biochimica et Biophysica Acta, General Subjects, Elsevier, vol. 1760, No. 6, 2006, pp. 877-882.
Sato, et al., "Studies on Pyrazines. 17. An Efficient Synthesis of Pteridine-6-carboxylic Acids", Journal of Heterocyclic Chemistry, Vo. 25, No. 6, Nov.-Dec. 1988, pp. 1737-1740.
Pfleiderer, "Transformation of Biopterin into Sepiapterin and Absolute Configuration of Sepiapterin, Chemische Berichte", vol. 112, No. 7, with partial English translation, 1979, pp. 2750-2755.
Nair, et al., "Folate Analogues. 31. Synthesis of the Reduced Derivatives of 11-Deazahomofolic Acid, 10-Methyl-11-deazahomofolic Acid, and Their Evaluation as Inhibitors of Glycinamide Ribonucleotide Formyltransferase", Journal of Medicinal Chemistry, vol. 32, No. 6, 1989, pp. 1277-1283.
Sugiura, et al., "Synthesis of Sepiapterin", Journal of the Chemical Society of Japan, No. 1, with partial English translation, 1972, pp. 206-208.
Schircks, et al., "Preparation of (6R,S)-5,6,7,8-Tetrahydro-L-Biopterine, 7,8-Dihydro-L-biopterine, L-Sepiapterine, Deoxysepiapterine, (6R,S)-5,6-Dihydrodeoxysepiapterine and 2'-Deoxybiopterine", Helvetica Chimica Acta, vol. 61 (7), with partial English translation, 1978, 5 pages.
Katoh, et al., "Cytochrome c-catalyzed Oxidation of Sepiapterin to 6-Lactylpterin", Zoological Magazine, 86, 1977, 3 pages.
Pteridines, vol. 23, 15th International Symposium on Pteridines and Folates, 2012, 2 pages.

*Primary Examiner* — Jeffrey H Murray
(74) *Attorney, Agent, or Firm* — Oblon, McClelland, Maier & Neustadt, L.L.P.

(57) ABSTRACT

To provide a method for producing sepiapterin, lactoylpterin or tetrahydrolactoylpterin.
Sepiapterin, lactoylpterin and tetrahydrolactoylpterin are produced at high yield through the following reaction scheme.

6 Claims, No Drawings

METHOD FOR PRODUCING SEPIAPTERIN AND TETRAHYDROLACTOYLPTERIN

TECHNICAL FIELD

The present invention relates to a method for producing sepiapterin, lactoylpterin and tetrahydrolactoylpterin, which are useful pharmaceuticals.

BACKGROUND ART

Tetrahydrobiopterin (BH4, sapropterin) controls production of nitric monoxide by the mediation of an endothelial nitric oxide synthase (NOS). Therefore, BH4 is thought to be effective for treating or ameliorating various diseases and pathological conditions in relation to nitric monoxide generated by the mediation of NOS. Such diseases and conditions include, for example, Parkinson's disease, cerebral ischemia, spasm after subarachnoidal hemorrhage, cerebrovascular disorders (e.g., ischemia-reperfusion injury), myocarditis, coronary vasospasm, cardiac hypertrophy, arteriosclerosis, hypertension, thrombosis, infections, endotoxin shock, hepatic cirrhosis, hypertrophic pyloric stenosis, gastric mucosal injury, pulmonary hypertension, renal dysfunction, impotence and hypoglycemia.

Also, BH4 plays an important role in a biosynthesis pathway involving intracerebral neurotransmitters such as serotonin, dopamine, noradrenaline and adrenaline. Previous studies suggest that occurrence of BH4 deficiency in cells causes brain dysfunctions. Such brain dysfunctions include central mental disorders (e.g., phenylketonuria, depression, hyperphagia, autism, attention deficit disorder and cognition disorder) and central movement disorders (e.g., myotonia, stiffness and tremor). However, in the case of peripheral administration, BH4 is blocked by the blood-brain barrier and cannot reach cerebral nervous cells. In this case, the above conditions are not ameliorated.

A recent study has revealed that, as compared with BH4, sepiapterin can more readily pass through the blood-brain barrier to easily enter the tissue. The study has reported that peripherally administered sepiapterin passes through the blood-brain barrier and is converted into BH4 in the brain, whereby elevating the brain BH4 level, and that sepiapterin serves as a useful therapeutic and prophylactic drug for brain dysfunctions (Patent Document 1).

Although BH4 has a wide range of physiological activities, the solubility thereof is considerably high. Thus, a considerable amount of BH4 administered is immediately discharged into urea. Therefore, sepiapterin, which can be readily taken into cells, is thought to have higher bioavailability than BH4. In addition, sepiapterin, which is a naturally occurring product, and its analogues, lactoylpterin and tetrahydrolactoylpterin, have high safety and are envisaged to exhibit various bioactivities.

Sepiapterin is known to be synthesized through a method involving reaction of 7,8-dihydropterin with α-keto-β-hydroxybutyric acid in the presence of zinc chloride (Non-Patent Document 1), and a method involving air-oxidation of BH4 for 6 days (Non-Patent Document 2).

Lactoylpterin is known to be synthesized through oxidation of sepiapterin (Non-Patent Documents 3 and 4).

CITATION LIST

Patent Documents

Patent Document 1: WO2011/132435

Non-Patent Documents

Non-Patent Document 1: Nippon Kagaku Kaishi (Journal of the Chemical Society of Japan), 206-208 (1972)
Non-Patent Document 2: Helvetica Chimica Acta, 61(7), 2731 (1978)
Non-Patent Document 3: Zoological Magazine 86, 29 (1977)
Non-Patent Document 4: Biochemical Genetics 17, 351 (1979)

SUMMARY OF THE INVENTION

Problems to be Solved by the Invention

When the method disclosed in Non-Patent Document 1 is employed, only a trace amount of sepiapterin is produced. Thus, the method cannot consistently produce sepiapterin. The method disclosed in Non-Patent Document 2 employs BH4, which is a very expensive material. Thus, the method cannot consistently produce sepiapterin on the industrial scale. In the method disclosed in Non-Patent Document 2, there are problems that a long reaction time is required and large amounts of by-products including biopterin (formed by oxidation of BH4) and deoxysepiapterin (formed via elimination of hydroxyl group at β-position of the side-chain). Also, the lactoylpterin synthesis methods disclosed in Non-Patent Documents 3 and 4 employ, as a raw material, sepiapterin, which is not readily available in the industry, and attain low yield. Thus, these methods cannot consistently produce sepiapterin.

In view of the foregoing, an object of the present invention is to provide a novel method for producing sepiapterin, lactoylpterin and tetrahydrolactoylpterin, which have recently been identified to serve as useful pharmaceuticals, the method being able to consistently supply these compounds.

Means for Solving the Problem

The present inventors have studied a method for synthesizing sepiapterin, lactoylpterin or tetrahydrolactoylpterin by use of available raw materials, and have found that sepiapterin, lactoylpterin and tetrahydrolactoylpterin can be produced at high yield by use of a compound represented by the following formula (1) or (7) as a starting material, resulting in the first consistent supply of these produced compounds as pharmaceuticals. The present invention has been accomplished on the basis of this finding.

Accordingly, the present invention relates to the following [1] to [32].

[1] A method for producing sepiapterin represented by formula (3):

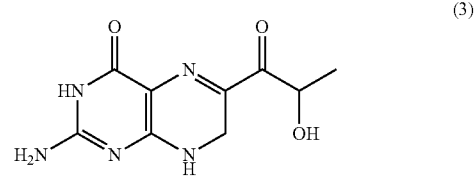 [SMILES: CC(O)C(=O)C1=Nc2c(nc(N)[nH]c2=O)NC1]

or a salt thereof, comprising subjecting, to reduction, lactoylpterin represented by formula (2):

or a salt thereof.

[2] The method as described in [1], wherein the reduction reaction is reduction by use of a sulfite, a hyposulfite or a thiosulfate, or catalytic reduction under basic conditions.

[3] A method for producing sepiapterin represented by formula (3):

(3)

or a salt thereof, comprising subjecting, to oxidation, tetrahydrolactoylpterin represented by formula (4):

(4)

or a salt thereof.

[4] The method as described in [3], wherein the oxidation reaction is oxidation by use of a peracid, or air oxidation under neutral or basic conditions.

[5] A method for producing tetrahydrolactoylpterin represented by formula (4):

(4)

or a salt thereof, comprising subjecting, to reduction, lactoylpterin represented by formula (2):

(2)

or a salt thereof.

[6] The method as described in [5], wherein the reduction reaction is reduction by use of a BH$_3$-based reducing agent, or catalytic reduction under basic conditions.

[7] The method as described in [5], wherein the reduction reaction is reduction by use of a BH$_3$-based reducing agent under acidic conditions, or catalytic reduction under basic conditions.

[8] A method for producing sepiapterin represented by formula (3):

(3)

or a salt thereof, comprising subjecting, to reduction, lactoylpterin represented by formula (2):

(2)

or a salt thereof, to thereby form tetrahydrolactoylpterin represented by formula (4):

(4)

or a salt thereof and, subsequently, subjecting the compound (4) to oxidation.

[9] The method as described in [8], wherein the reduction reaction is reduction by use of a BH$_3$-based reducing agent, or catalytic reduction under basic conditions, and the oxidation reaction is oxidation by use of a peracid, or air oxidation under neutral or basic conditions.

[10] The method as described in [9], wherein the reduction reaction is reduction by use of a BH$_3$-based reducing agent under acidic conditions, or catalytic reduction under basic conditions.

[11] A method for producing sepiapterin represented by formula (3):

(3)

or a salt thereof, comprising subjecting, to deprotection, a compound represented by formula (5):

(5)

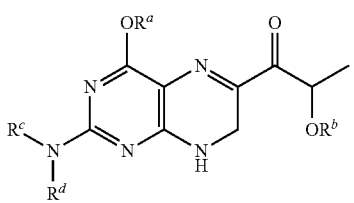

wherein $R^a$ and $R^b$, which are identical to or different from each other, each represent a protective group, and each of $R^c$ and $R^d$ represents a hydrogen atom or a protective group.

[12] The method as described in [11], wherein the deprotection reaction is hydrolysis or solvolysis in the presence of a base or an acid having a pKa of 12 or lower, or deprotection by use of a fluoride anion.

[13] A method for producing sepiapterin represented by formula (3):

(3)

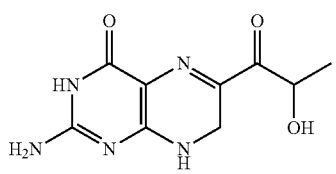

or a salt thereof, comprising subjecting, to oxidation, a compound represented by formula (8):

(8)

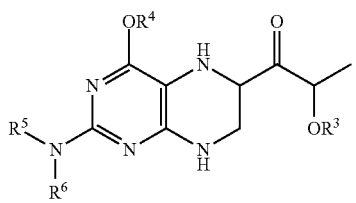

wherein $R^3$, $R^4$ and $R^5$, which are identical to or different from one another, each represent a protective group, and $R^6$ represents a hydrogen atom or a protective group, to thereby form a compound represented by formula (5-1):

(5-1)

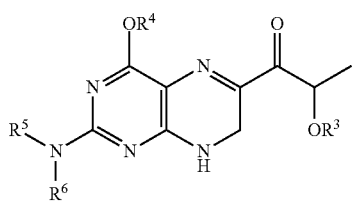

wherein $R^3$, $R^4$, $R^5$ and $R^6$ have the same meaning as defined above and, subsequently, subjecting the formed compound to deprotection.

[14] The method as described in [13], wherein the oxidation reaction is oxidation by use of a peracid, or air oxidation under neutral or basic conditions, and the deprotection reaction is hydrolysis or solvolysis in the presence of a base or an acid having a pKa of 12 or lower, or deprotection by use of a fluoride anion.

[15] A method for producing sepiapterin represented by formula (3):

(3)

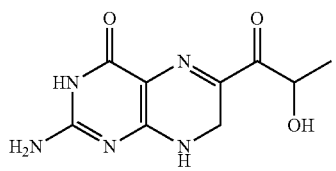

or a salt thereof, comprising subjecting, to reduction, a compound represented by formula (7):

(7)

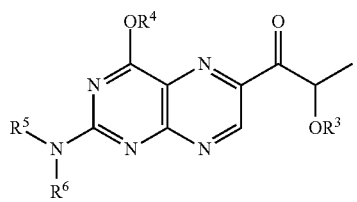

wherein $R^3$, $R^4$ and $R^5$, which are identical to or different from one another, each represent a protective group, and $R^6$ represents a hydrogen atom or a protective group, to thereby form a compound represented by formula (5-1):

(5-1)

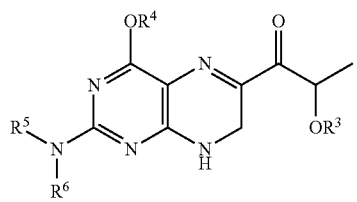

wherein $R^3$, $R^4$, $R^5$ and $R^6$ have the same meaning as defined above and, subsequently, subjecting the formed compound to deprotection.

[16] The method as described in [15], wherein the reduction reaction is reduction by use of a sulfite, a hyposulfite or a thiosulfate, or catalytic reduction under basic conditions, and the deprotection reaction is hydrolysis or solvolysis in the presence of a base or an acid having a pKa of 12 or lower, or deprotection by use of a fluoride anion.

[17] A method for producing sepiapterin represented by formula (3):

(3)

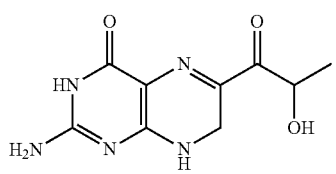

or a salt thereof, comprising subjecting, to reduction, a compound represented by formula (7):

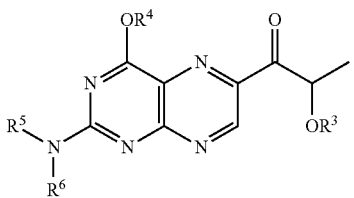

(7)

wherein $R^3$, $R^4$ and $R^5$, which are identical to or different from one another, each represent a protective group, and $R^6$ represents a hydrogen atom or a protective group, to thereby form a compound represented by formula (8):

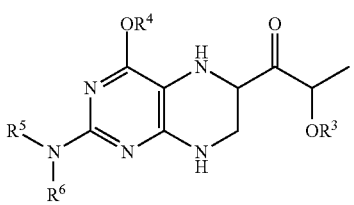

(8)

wherein $R^3$, $R^4$, $R^5$ and $R^6$ have the same meaning as defined above; subjecting the compound (8) to oxidation, to thereby form a compound represented by formula (5-1):

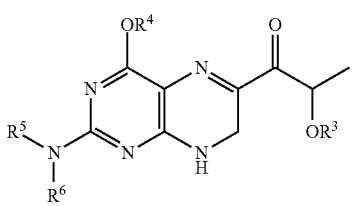

(5-1)

wherein $R^3$, $R^4$, $R^5$ and $R^6$ have the same meaning as defined above; and, subsequently, subjecting the formed compound to deprotection.

[18] The method as described in [17], wherein the reduction reaction is reduction by use of a sulfite, a hyposulfite or a thiosulfate, or catalytic reduction under basic conditions; the oxidation reaction is oxidation by use of a peracid, or air oxidation under neutral or basic conditions; and the deprotection reaction is hydrolysis or solvolysis in the presence of a base or an acid having a pKa of 12 or lower, or deprotection by use of a fluoride anion.

[19] A method for producing sepiapterin represented by formula (3):

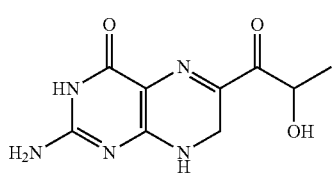

(3)

or a salt thereof, comprising subjecting, to reduction, a compound represented by formula (1):

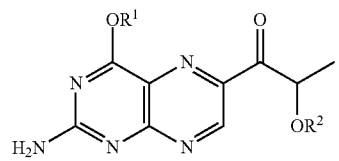

(1)

wherein $R^1$ and $R^2$, which are identical to or different from each other, each represent a protective group, to thereby form a compound represented by formula (5-2):

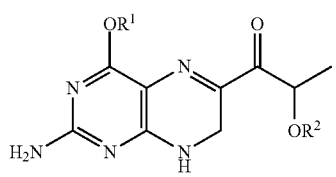

(5-2)

wherein $R^1$ and $R^2$ have the same meaning as defined above and, subsequently, subjecting the compound (5-2) to deprotection.

[20] The method as described in [19], wherein the reduction reaction is reduction by use of a sulfite, a hyposulfite or a thiosulfate, or catalytic reduction under basic conditions, and the deprotection reaction is hydrolysis or solvolysis in the presence of a base or an acid having a pKa of 12 or lower, or deprotection by use of a fluoride anion.

[21] A method for producing sepiapterin represented by formula (3):

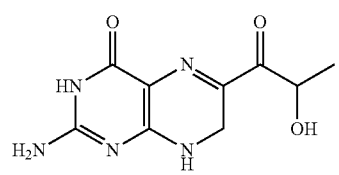

(3)

or a salt thereof, comprising subjecting, to deprotection, a compound represented by formula (8):

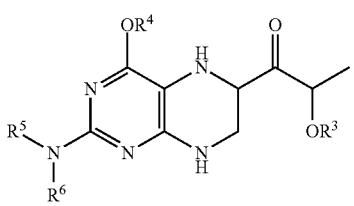

(8)

wherein $R^3$, $R^4$, and $R^5$, which are identical to or different from one another, each represent a protective group, and $R^6$ represents a hydrogen atom or a protective group, to thereby form tetrahydrolactoylpterin represented by formula (4):

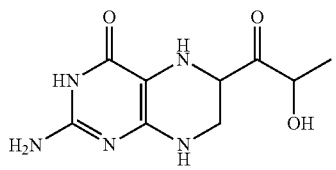
(4)

and subjecting the compound (4) to oxidation.

[22] The method as described in [21], wherein the deprotection reaction is hydrolysis or solvolysis in the presence of a base or an acid having a pKa of 12 or lower, or deprotection by use of a fluoride anion, and the oxidation reaction is oxidation by use of a peracid, or air oxidation under neutral or basic conditions.

[23] A method for producing sepiapterin represented by formula (3):

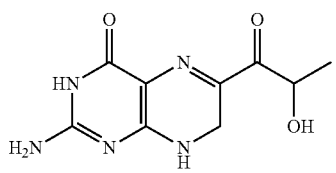
(3)

or a salt thereof, comprising subjecting, to reduction, a compound represented by formula (7):

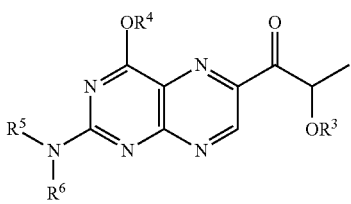
(7)

wherein $R^3$, $R^4$ and $R^5$, which are identical to or different from one another, each represent a protective group, and $R^6$ represents a hydrogen atom or a protective group, to thereby form a compound represented by formula (8):

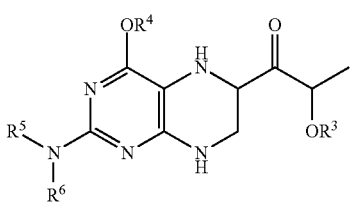
(8)

wherein $R^3$, $R^4$, $R^5$ and $R^6$ have the same meaning as defined above; subsequently, subjecting the compound (8) to deprotection, to thereby form tetrahydrolactoylpterin represented by formula (4):

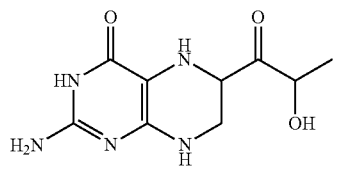
(4)

and subjecting the compound (4) to oxidation.

[24] A production method as described in [23], wherein the reduction reaction is reduction by use of a sulfite, a hyposulfite or a thiosulfate, or catalytic reduction under basic conditions; the deprotection reaction is hydrolysis or solvolysis in the presence of a base or an acid having a pKa of 12 or lower, or deprotection by use of a fluoride anion; and the oxidation reaction is oxidation by use of a peracid, or air oxidation under neutral or basic conditions.

[25] A method for producing sepiapterin represented by formula (3):

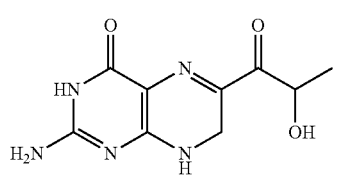
(3)

or a salt thereof, comprising subjecting, to deprotection, a compound represented by formula (1):

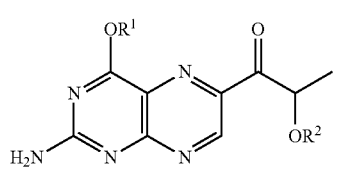
(1)

wherein $R^1$ and $R^2$, which are identical to or different from each other, each represent a protective group, to thereby form lactoylpterin represented by formula (2):

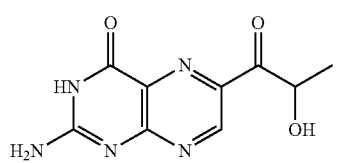
(2)

and subjecting the compound (2) to reduction.

[26] The method as described in [25], wherein the deprotection reaction is hydrolysis or solvolysis in the presence of a base or an acid having a pKa of 12 or lower, or deprotection by use of a fluoride anion, and the reduction reaction is reduction by use of a sulfite, a hyposulfite or a thiosulfate, or catalytic reduction under basic conditions.

[27] A method for producing lactoylpterin represented by formula (2):

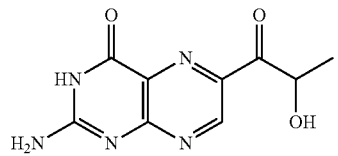

(2)

or a salt thereof, comprising subjecting, to deprotection, a compound represented by formula (1):

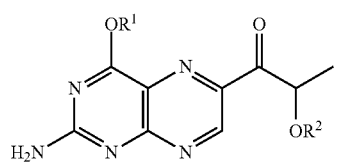

(1)

wherein $R^1$ and $R^2$, which are identical to or different from each other, each represent a protective group.

[28] The method as described in [27], wherein the deprotection reaction is hydrolysis or solvolysis in the presence of a base or an acid having a pKa of 12 or lower, or deprotection by use of a fluoride anion.

[29] A method for producing tetrahydrolactoylpterin represented by formula (4):

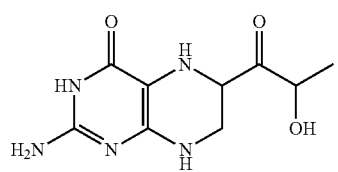

(4)

or a salt thereof, comprising subjecting, to deprotection, a compound represented by formula (8):

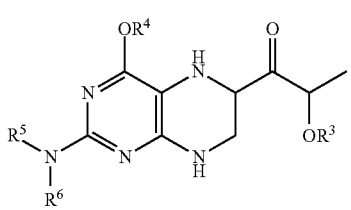

(8)

wherein $R^3$, $R^4$ and $R^5$, which are identical to or different from one another, each represent a protective group, and $R^6$ represents a hydrogen atom or a protective group).

[30] The method as described in [29], wherein the deprotection reaction is hydrolysis or solvolysis in the presence of a base or an acid having a pKa of 12 or lower, or deprotection by use of a fluoride anion.

[31] A method for producing tetrahydrolactoylpterin represented by formula (4):

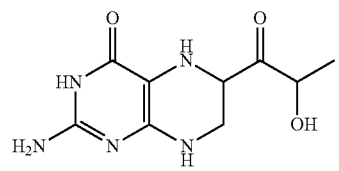

(4)

or a salt thereof, comprising subjecting, to reduction, a compound represented by formula (7):

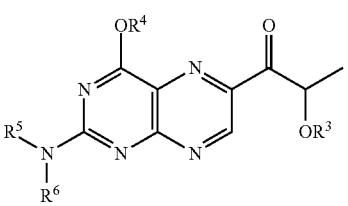

(7)

wherein $R^3$, $R^4$ and $R^5$, which are identical to or different from one another, each represent a protective group, and $R^6$ represents a hydrogen atom or a protective group, to thereby form a compound represented by formula (8):

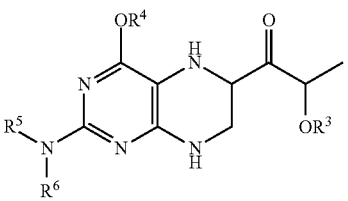

(8)

wherein $R^3$, $R^4$, $R^5$ and $R^6$ have the same meanings as defined above, and subjecting the compound (8) to deprotection.

[32] The method as described in [31], wherein the reduction reaction is reduction by use of a sulfite, a hyposulfite or a thiosulfate, or catalytic reduction under basic conditions, and the deprotection reaction is hydrolysis or solvolysis in the presence of a base or an acid having a pKa of 12 or lower, or deprotection by use of a fluoride anion.

Effects of the Invention

According to the present invention, sepiapterin, lactoylpterin and tetrahydrolactoylpterin, which are useful pharmaceuticals, can be produced at high yield from readily available raw materials.

MODES FOR CARRYING OUT THE INVENTION

The method of the present invention is represented by the following reaction scheme:

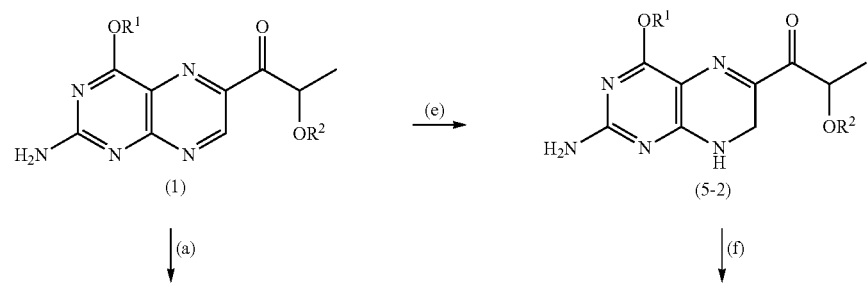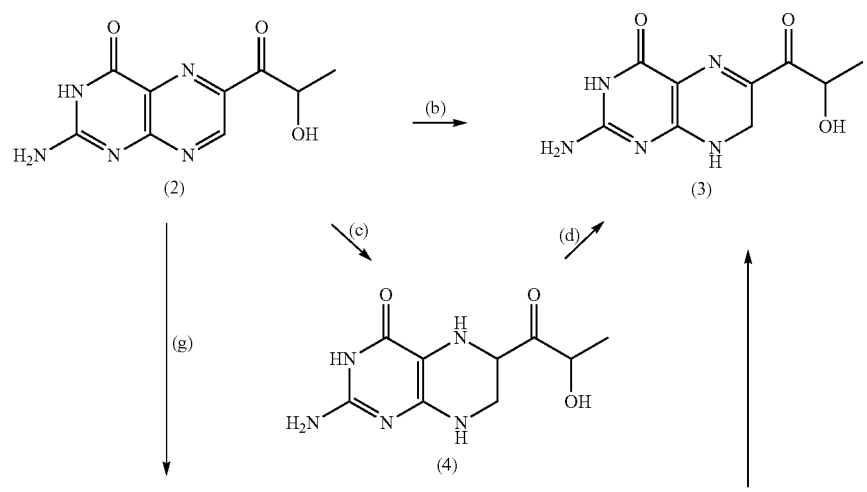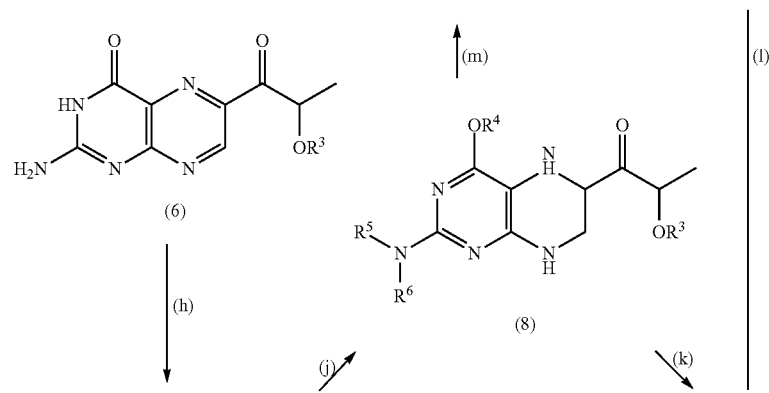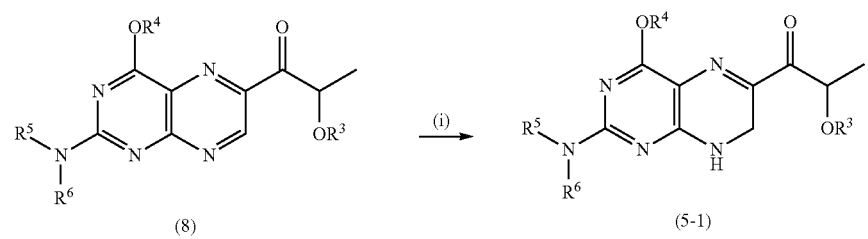

In the reaction scheme, $R^1$, $R^2$, $R^3$, $R^4$, $R^5$, and $R^6$ have the same meanings as defined above.

The compound represented by formula (5) encompasses the compounds represented by formulas (5-1) and (5-2) shown in the reaction scheme. Thus, $R^a$, $R^b$, $R^c$ and $R^d$ correspond collectively to $R^1$, $R^2$, $R^3$, $R^4$, $R^5$ and $R^6$ of formula (5-1) and formula (5-2).

The compound represented by formula (7) may be produced from the compound represented by formula (1). Alternatively, the compound represented by formula (7) may be produced directly from the compound represented by formula (2).

The compounds in the above reaction scheme include an S-form, an R-form and an SR-form, in terms of configuration of the hydroxyl group. Also, tetrahydrolactoylpterin represented by formula (4) includes the following isomers.

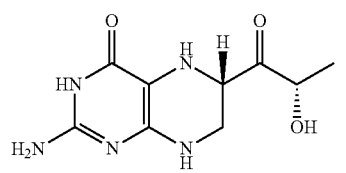
(4a)

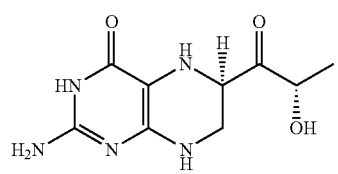
(4b)

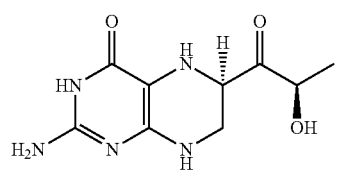
(4c)

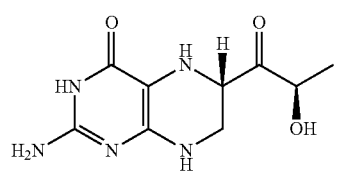
(4d)

Each of the protective groups represented by $R^1$ to $R^6$ is preferably eliminated through hydrolysis, solvolysis, deprotection with a fluoride anion or the like.

Examples of such protective groups include alkoxyalkyl, alkyl, acyl, silyl, alkoxycarbonyl and trityl.

Examples of the alkoxyalkyl group include $C_{1-6}$ alkoxy $C_{1-6}$ alkyl groups. Of these, methoxymethyl, ethoxymethyl, methoxyethoxymethyl, 2-tetrahydropyranyl and like groups are preferred. Examples of the alkyl group include $C_3$-$C_8$ linear, branched or cyclic alkyl groups. Of these, cyclopentyl, cyclohexyl, isopropyl, tert-butyl and like groups are preferred. Examples of the acyl group include formyl, $C_1$-$C_{12}$ linear, branched or cyclic alkylcarbonyl groups and $C_6$-$C_{14}$ arylcarbonyl groups. Of these, acetyl, benzoyl and like groups are preferred. Examples of the silyl group include tri $C_1$-$C_6$ alkylsilyl groups, alkyldiphenylsilyl groups and triphenylsilyl groups. Of these, trimethylsilyl, triethylsilyl, triisopropylsilyl, tert-butyldimethylsilyl, diphenylmethylsilyl, tert-butyldiphenylsilyl, triphenylmethyl and like groups are preferred. Examples of the alkoxycarbonyl group include $C_1$-$C_{14}$ alkoxycarbonyl groups. Of these, methoxycarbonyl, ethoxycarbonyl, tert-butoxycarbonyl, and benzyloxycarbonyl are preferred.

The protective groups of $R^1$ to $R^6$ may be identical to or different from one another.

Among these protective groups, examples of $R^1$ and $R^4$ include an alkoxyalkyl group, an alkyl group, an acyl group, a silyl group, an alkoxycarbonyl group and a trityl group. From the viewpoint of suppression of by-products, preferred are an alkoxyalkyl group, a branched or cyclic alkyl group, an acyl group, a silyl group, an alkoxycarbonyl group and a trityl group, serving as protective groups which are eliminated under neutral conditions or weakly basic to acidic conditions. More preferred are an alkoxyalkyl group, a branched or cyclic alkyl group, a silyl group, an alkoxycarbonyl group and a trityl group, serving as protective groups which are eliminated under acidic conditions. Examples of $R^2$ and $R^3$ include an alkoxyalkyl group, an alkyl group, an acyl group, a silyl group, an alkoxycarbonyl group and a trityl group. From the viewpoint of suppression of by-products, preferred are an alkoxyalkyl group, a branched or cyclic alkyl group, an acyl group, a silyl group, an alkoxycarbonyl group and a trityl group, serving as protective groups which are eliminated under neutral conditions or weakly basic to acidic conditions. More preferred are an alkoxyalkyl group, a branched or cyclic alkyl group, a silyl group, an alkoxycarbonyl group and a trityl group, serving as protective groups which are eliminated under acidic conditions. Examples of $R^5$ and $R^6$ include an alkoxyalkyl group, an alkyl group, an acyl group, an alkoxycarbonyl group and a trityl group. From the viewpoint of suppression of by-products, preferred are an alkoxyalkyl group, a branched or cyclic alkyl group, an acyl group, an alkoxycarbonyl group and a trityl group, serving as protective groups which are eliminated under neutral conditions or weakly basic to acidic condition. More preferred are an alkoxyalkyl group, an alkoxycarbonyl group and a trityl group, serving as protective groups which are eliminated under acidic condition.

The compound represented by formula (1), serving as a raw material, may be produced through, for example, the method disclosed in JP-A-2011-11976 (the application previously filed by the present inventors) or in Heterocycles 71(4), 911 (2007) as represented by the following reaction scheme.

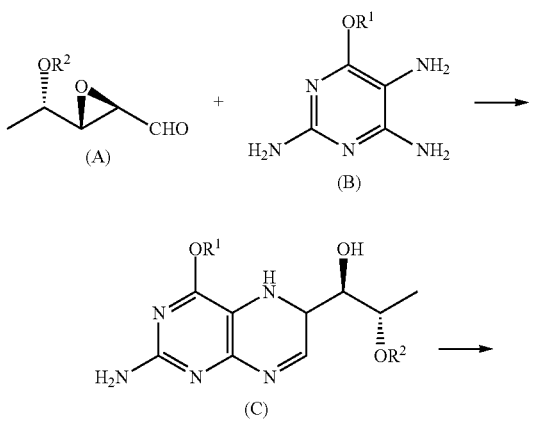

-continued

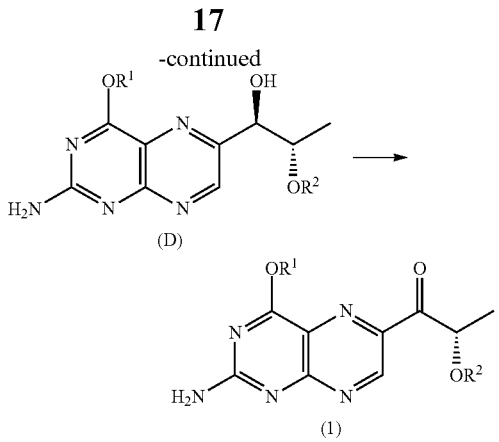

In the reaction scheme, $R^1$ and $R^2$ have the same meanings as defined above.

Accordingly, the compound represented by formula (1) may be produced by binding an epoxyaldehyde compound (A) to a compound represented by formula (B) in a polar solvent in the presence of an acid having a pKa of 4.5 or lower, to thereby form a compound represented by formula (C); oxidizing the compound represented by formula (C) by use of iodine and/or hydrogen peroxide, to thereby form a compound represented by formula (D); and oxidizing the compound represented by formula (D) with tetrapropylammonium perruthenate and 4-methylmorpholine N-oxide. The optically active epoxyaldehyde compound (A) may be produced through, for example, the method disclosed in Tetrahedron Letters 7847 (2004). When an R-lactic acid derivative is used as a raw material, a compound (A) having a different configuration of the 4-position (the protected hydroxyl group) can be produced. Thus, according to the present invention, sepiapterin, lactoylpterin and tetrahydrolactoylpterin, which have different configurations, can be selectively produced.

The steps (a) to (m) in the reaction scheme will next be described.

[Steps (a) and (f)]

Step (a) or (f) is a step of deprotecting the compound represented by formula (1) or (5-2). Deprotection may be performed through selecting an appropriate method depending on the type of the protective group, for example, hydrolysis, solvolysis or deprotection by use of a fluoride anion. From the viewpoint of suppression of by-products, hydrolysis and solvolysis are preferably performed under weakly basic, a neutral or an acidic conditions, with acidic conditions being more preferred. More specifically, hydrolysis and solvolysis are preferably performed in the presence of a base or an acid having a pKa of 12 or lower. More preferably, hydrolysis and solvolysis are performed in the presence of an acid having a pKa of 7 or lower.

Hydrolysis or solvolysis may be performed through a conventional method in a solvent such as water, a lower alcohol, dimethoxyethane, dioxane, THF, DMSO, nitromethane, acetone, ethyl acetate, toluene or acetic acid, or a mixture thereof at 0° C. to a reflux temperature. The reaction time is preferably 0.5 hours to 48 hours. Examples of the lower alcohol include $C_1$-$C_4$ alcohols such as methanol, ethanol and isopropanol. The amount of the solvent (e.g., water or a lower alcohol) used in the reaction may be an amount which allows a portion of the raw material compound to be dissolved. The amount is preferably 0.1 to 1,000 parts by mass, more preferably 0.1 to 50 parts by mass, with respect to 1 part by mass of the compound represented by formula (1) or (5-2).

Deprotection with a fluoride anion may be performed through a conventional method by use of, for example, a hydrofluoric acid compound such as hydrofluoric acid or hydrofluoric acid-pyridine complex, or an ammonium fluoride salt such as tetrabutylammonium fluoride. The deprotection reaction may be performed in a solvent such as water, a lower alcohol, dimethoxyethane, dioxane, THF, DMSO, nitromethane, acetone, ethyl acetate, toluene or acetic acid, or a mixture thereof at 0° C. to a reflux temperature. The reaction time is preferably 0.5 hours to 48 hours.

Examples of the additive used in hydrolysis and solvolysis include inorganic bases such as sodium hydroxide, potassium hydroxide, potassium carbonate, sodium carbonate, sodium hydrogencarbonate, potassium hydrogencarbonate, potassium acetate, potassium t-butoxide, potassium phosphate and aqueous ammonia; organic bases such as imidazole, trimethylamine, triethylamine, diethylamine, propylamine, tetramethylammonium hydroxide, aniline, N,N-dimethylaniline, dimethylaminopyridine and diazabicycloundecene; inorganic acids such as hydrochloric acid, sulfuric acid, nitric acid, nitrous acid, chloric acid, perchloric acid, phosphoric acid and hydrobromic acid; and organic acids such as acetic acid, oxalic acid, formic acid, trifluoroacetic acid, methanesulfonic acid and p-toluenesulfonic acid. From the viewpoint of suppression of by-products, preferred is addition of a base or an acid having a pKa of 12 or lower; such as potassium carbonate, sodium carbonate, sodium hydrogencarbonate, potassium hydrogencarbonate, potassium acetate, potassium phosphate, aqueous ammonia, trimethylamine, triethylamine, diethylamine, propylamine or N,N-dimethylaniline. Addition of an acid having a pKa of 7 or lower is more preferred. These acids and bases may be used singly or in combination of two or more species.

Of these, an inorganic acid is preferred, with hydrochloric acid being particularly preferred. The amount of the additive is preferably 0.1 to 100 parts by mass, more preferably 0.1 to 50 parts by mass, with respect to 1 part by mass of the compound represented by formula (1) or (5-2).

In steps (a) and (f), when the protective groups $R^1$ and $R^2$ are different from each other, different deprotection treatments suited for respective protective groups may be performed. The deprotection treatments may be performed sequentially or simultaneously.

[Steps (b) and (e)]

Step (b) or (e) is a stept of reducing the compound represented by formula (2) to produce the compound represented by formula (3), or reducing the compound represented by formula (1) to produce the compound represented by formula (5-2). Through the reduction, the 7,8-double bond of the pterin skeleton is selectively reduced.

The reduction is carried out by use of a reducing agent or through catalytic reduction (hydrogenation in the presence of a catalyst). Examples of the reducing agent include a sulfite, a hyposulfite, a thiosulfate, a hydride reducing agent and a reducing metal. Examples of the sulfite include sodium sulfite ($Na_2SO_3$) and potassium sulfite ($K_2SO_3$). Examples of the hyposulfite include sodium hyposulfite ($Na_2S_2O_4$) and potassium hyposulfite ($K_2S_2O_4$). Examples of the thiosulfate include sodium thiosulfate ($Na_2S_2O_3$) and potassium thiosulfate ($K_2S_2O_3$). Examples of the hydride reducing agent include $NaBH_4$, $NaBH_3CN$, $NaB(OAc)_{1-3}Hx$, $NaB(OMe)_{1-3}Hx$, $LiBH_4$, $LiBH(Et)_3$, L-Selectride, K-Selectride and $LiAlH_4$ (wherein x is an integer of 1 to 3). Examples of the reducing metal include Zn, Fe, Ni, Hg, Al and Mg. Among these reducing agents, a sulfite, a hyposulfite and a thiosulfate are more preferred.

In one embodiment, reduction by use of a reducing agent is performed in a solvent such as water, methanol, ethanol, dimethoxyethane, dioxane, dimethylformamide, dimethylacetamide, THF, DMSO, nitromethane, acetone, ethyl acetate or acetic acid, at 0° C. to 100° C. for 0.5 hours to 24 hours. The reducing agent is added in an amount of 0.5 to 20 mol, with respect to 1 mol of the compound represented by formula (1) or (2).

Examples of the catalyst employed in catalytic reduction (hydrogenation in the presence of a catalyst) include Pd, Ru, Rh, Pt, Ni and Cu. Of these, Pd and Pt are more preferred. Such a metal may be supported on a carrier such as carbon. Alternatively, PdO, Pd(OH)$_2$ and a metal poisoned by a nitrogen compound (e.g., ethylenediamine), a sulfur compound (e.g., Ph$_2$S) or the like may also be used.

The catalytic reduction (hydrogenation in the presence of a catalyst) may be performed in a solvent such as water, an alcohol including methanol or ethanol, dimethoxyethane, dioxane, dimethylformamide, dimethylacetamide, THF, DMSO, nitromethane, acetone, ethyl acetate, toluene or acetic acid. In the case of the compound represented by formula (1), an alcohol, THF, ethyl acetate or toluene is preferred, whereas in the case of the compound represented by formula (2), water, an alcohol or dimethylformamide is preferred. In one embodiment, the catalyst is used in an amount of 0.01 to 5 parts by mass, preferably 0.1 to 2 parts by mass, with respect to 1 part by mass of the relevant compound. The hydrogen pressure is normal pressure to 10 MPa, preferably normal pressure to 0.5 MPa. The reaction temperature is 0 to 80° C., preferably 20 to 50° C. The reaction time is 1 to 72 hours, preferably 1 to 24 hours.

Also, the catalytic reduction (hydrogenation in the presence of a catalyst) is preferably performed under basic conditions realized through addition of a base, from the viewpoints of selectivity of reaction and yield of the target product. Examples of the base include inorganic bases such as sodium hydroxide, potassium hydroxide, potassium carbonate, sodium carbonate, sodium hydrogencarbonate, potassium hydrogencarbonate, potassium acetate, potassium t-butoxide, potassium phosphate and aqueous ammonia; and organic bases such as imidazole, trimethylamine, triethylamine, diethylamine, propylamine, tetramethylammonium hydroxide, aniline, N,N-dimethylaniline, dimethylaminopyridine and diazabicycloundecene. From the viewpoint of suppression of by-products, preferred is addition of an inorganic base having a pKa of 8 to 12; such as potassium carbonate, sodium carbonate, sodium hydrogencarbonate, potassium hydrogencarbonate, potassium acetate, potassium phosphate or aqueous ammonia, or addition of an organic base having a pKa of 8 to 12; such as trimethylamine, triethylamine, diethylamine, propylamine or N,N-dimethylaniline. More preferably, aqueous ammonia, or an organic base having a pKa of 8 to 12; such as trimethylamine, triethylamine, diethylamine, propylamine or N,N-dimethylaniline is preferably added. These bases may be used singly or in combination of two or more species. The base is preferably used in an amount 0.1 to 150 mol, more preferably 1 to 50 mol, with respect to 1 mol of the compound represented by formula (1) or (2).

Among these reductions, use of a sulfite, a hyposulfite or a thiosulfate, or catalytic reduction (hydrogenation in the presence of a catalyst) is more preferred, from the viewpoints of reaction yield and suppression of by-products.

[Step (c)]

Step (c) is a step of reducing lactoylpterin represented by formula (2), while the lactoylpterin remains non-protected, to thereby produce tetrahydrolactoylpterin (4) or a salt thereof.

The reduction is preferably performed by use of a BH$_3$-based reducing agent or through catalytic reduction under basic conditions, from the viewpoint of selective production of tetrahydrolactoylpterin (4). When reduction by use of a BH$_3$-based reducing agent or catalytic reduction under basic conditions is performed, the pteridine ring is preferentially reduced, but reduction of the carbonyl group in the lactoyl group can be prevented. Also, elimination of the hydroxyl group at the β-position with respect to the lactoyl group can be prevented. Examples of the BH$_3$-based reducing agent include B$_2$H$_6$, THF-BH$_3$, NH$_3$—BH$_3$, Et$_3$-NBH$_3$, DEA-BH$_3$, DIEA-BH$_3$, SMe$_2$-BH$_3$, PPh$_3$-BH$_3$, Py-BH$_3$, Pic-BH$_3$ and morpholine-BH$_3$. Among them, amine compound-BH$_3$ such as Py-BH$_3$, Pic-BH$_3$ and Et$_3$N—BH$_3$ are particularly preferred.

The reduction by use of a BH$_3$-based reducing agent preferably performed under acidic conditions. Examples of the acid include inorganic acids such as hydrochloric acid, sulfuric acid, nitric acid, nitrous acid, chloric acid, perchloric acid, phosphoric acid and hydrobromic acid; and organic acids such as acetic acid, oxalic acid, formic acid, trifluoroacetic acid, methanesulfonic acid and p-toluenesulfonic acid. However, the reduction is more preferably performed in the presence of an acid having a pKa of 7 or lower such as hydrochloric acid or p-toluenesulfonic acid. From the viewpoints of availability and the like, the reduction is more preferably performed in the presence of hydrochloric acid. The reduction may be performed in a solvent such as water, an alcohol (e.g., methanol or ethanol) or tetrahydrofuran. More preferably, the solvent is water, an alcohol (e.g., methanol or ethanol) or a mixture thereof. In one embodiment, the reaction is performed at −20 to 80° C., more preferably −20 to 10° C., for 0.5 to 24 hours.

The catalytic reduction under basic conditions is preferably performed under the same conditions as employed in catalytic reduction of step (b) or (e). In other words, the catalyst employed, reaction solvent, reaction temperature and reaction time are the same as employed in step (b) or (e). In addition, means for realizing basic conditions is the same as employed in step (b) or (e).

[Step (d)]

Step (d) is a step of oxidizing the compound represented by formula (4), to thereby form sepiapterin (3).

The oxidation is performed by use of an oxidizing agent or through oxygen oxidation. Examples of the oxidizing agent include a metallic oxidizing agent such as chromic acid or a manganese compound; organic compounds such as DMSO, quinone, acetone, a hypervalent iodine compound and TEMPO; and peracids such as hydrogen peroxide, peracetic acid and perbenzoic acid. Oxygen oxidation is performed by means of air, oxygen, ozone or the like. The oxygen oxidation may be performed in the presence of a catalyst such as Pd, Ru, Rh, Pt, Ni or Cu. Among the oxidation processes, oxidation by use of a peracid or oxygen oxidation by means of air is preferred. More preferably, oxidation by use of a peracid, or oxygen oxidation by means of air under neutral or basic conditions is performed.

The oxygen oxidation with air is preferably performed under neutral or basic conditions. In the case of neutral conditions, the oxidation is performed by stirring in a solvent such as water, an alcoholic solvent (e.g., methanol or ethanol), dimethoxyethane, dioxane, dimethylformamide, dimethylacetamide, THF, DMSO, nitromethane, acetone or ethyl acetate, preferably water or an alcohol, under air, for 1 to 72 hours. In the case of basic conditions, a base is added. Examples of the base include inorganic bases such as sodium hydroxide, potassium hydroxide, potassium carbonate, sodium carbonate, sodium hydrogencarbonate, potassium hydrogencarbonate, potassium acetate, potassium t-butoxide, potassium phosphate and aqueous ammonia; organic bases such as imidazole, trimethylamine, triethylamine, diethylamine, propylamine, tetramethylammonium hydroxide, aniline, N,N-dimethylaniline, dimethylaminopyridine and diazabicycloundecene.

Examples of the peracid employed in the oxidation include peracids such as hydrogen peroxide, peracetic acid and perbenzoic acid. Of these, hydrogen peroxide is more preferred. The amount of the peracid employed in the oxidation is preferably 0.5 to 3 mol, more preferably 0.9 to 1.1 mol, with respect to 1 mol of the compound represented by formula (4). In one embodiment, the oxidation is performed in a solvent such as water, an alcoholic solvent (e.g., methanol or ethanol), dimethoxyethane, dioxane, dimethylformamide, dimethylacetamide, THF, DMSO, nitromethane, acetone, ethyl acetate or acetic acid. The solvent is preferably water or an alcohol. The oxidation is performed at −15° C. to 60° C., preferably −15° C. to 10° C., for 1 to 24 hours.

[Step (g)]

Step (g) is a step of reacting the compound represented by formula (2) with $R^3X$, wherein X represents a leaving group and $R^3$ has the same meaning as defined above, to thereby produce the compound represented by formula (6).

Examples of $R^3X$ for providing a target compound with a protective group include a halide or an acid anhydride of $R^3$ of the aforementioned protective group. Examples of the leaving group in $R^3X$ include a halogen atom and an acid anhydride residue.

The reaction between the compound represented by formula (2) and $R^3X$ is preferably performed under neutral conditions or in the presence of an inorganic base such as sodium hydroxide, potassium hydroxide, potassium carbonate, sodium carbonate, sodium hydrogencarbonate, potassium hydrogencarbonate, potassium acetate, potassium t-butoxide, potassium phosphate or aqueous ammonia, or an organic base such as imidazole, trimethylamine, triethylamine, diethylamine, propylamine, tetramethylammonium hydroxide, aniline, N,N-dimethylaniline, dimethylaminopyridine and diazabicycloundecene. From the viewpoint of suppression of by-products, the reaction is more preferably performed under neutral conditions or in the presence of a base having a pKa of 8 to 12 such as potassium carbonate, sodium carbonate, sodium hydrogencarbonate, potassium hydrogencarbonate, potassium acetate, potassium phosphate, aqueous ammonia, trimethylamine, triethylamine, diethylamine, propylamine or N,N-dimethylaniline. These bases may be used singly or in combination of two or more species. The amount of the base used in the reaction is preferably 0.01 to 10 mol, more preferably 0.05 to 3 mol, with respect to 1 mol of the compound represented by formula (2). The amount of $R^3X$ used in the reaction is preferably 1 to 10 mol, more preferably 1 to 5 mol, with respect to 1 mol of the compound represented by formula (2).

In one embodiment, the reaction is performed in a polar solvent such as dimethylformamide, dimethylacetamide, ethyl acetate, acetone, tetrahydrofuran, acetonitrile, N-methylpyrrolidone or HMPA, at 0° C. to a reflux temperature, for 30 minutes to 5 hours.

[Step (h)]

Step (h) is a step of reacting the compound represented by formula (6) with $R^4X$, $R^5X$ and $R^6X$, wherein $R^4$ and X have the same meanings as defined above, to thereby produce the compound represented by formula (7).

$R^4X$, $R^5X$ and $R^6X$ for providing a target compound with a protective group may be a halide or an acid anhydride of $R^4$, $R^5$ and $R^6$ of the aforementioned protective group.

The reaction of the compound represented by formula (6) with $R^4X$, $R^5X$ and $R^6X$ is preferably performed under neutral conditions or in the presence of an inorganic base such as sodium hydroxide, potassium hydroxide, potassium carbonate, sodium carbonate, sodium hydrogencarbonate, potassium hydrogencarbonate, potassium acetate, potassium t-butoxide, potassium phosphate or aqueous ammonia, or an organic base such as imidazole, trimethylamine, triethylamine, diethylamine, propylamine, tetramethylammonium hydroxide, aniline, N,N-dimethylaniline, dimethylaminopyridine and diazabicycloundecene. From the viewpoint of suppression of by-products, the reaction is more preferably performed under neutral conditions or in the presence of a base having a pKa of 8 to 12 such as potassium carbonate, sodium carbonate, sodium hydrogencarbonate, potassium hydrogencarbonate, potassium acetate, potassium phosphate, aqueous ammonia, trimethylamine, triethylamine, diethylamine, propylamine or N,N-dimethylaniline. These bases may be used singly or in combination of two or more species. The amount of the base used in the reaction is preferably 0.01 to 10 mol, more preferably 0.05 to 5 mol, with respect to 1 mol of the compound represented by formula (6). The amount of each of $R^4X$, $R^5X$ and $R^6X$ used in the reaction is preferably 1 to 10 mol, more preferably 2 to 5 mol, with respect to 1 mol of the compound represented by formula (6).

In one embodiment, the reaction is performed in a polar solvent such as dimethylformamide, dimethylacetamide, ethyl acetate, acetone, tetrahydrofuran, acetonitrile, N-methylpyrrolidone or HMPA, at 0° C. to a reflux temperature, for 30 minutes to 5 hours.

In the case where $R^4X$, $R^5X$ and $R^6X$ are identical to one another, step (g) may be performed in a one-step reaction. In the case where $R^4X$, $R^5X$ and $R^6X$ are different from one another, step (g) is performed in a 2-step or 3-step reaction.

[Direct Reaction in Steps (g) and (h)]

The compound represented by formula (7) may be produced by simultaneously protecting, with the same protective groups, all of the hydroxyl group, ketone groups and amino group of the compound represented by formula (2). Alternatively, the compound represented by formula (7) may be produced by reacting the compound represented by formula (1) with $R^5X$ and $R^6X$.

These protective group introduction may be performed under the same conditions as employed in step (g) and step (h).

[Step (j)]

Step (j) is a step of reducing the compound represented by formula (7), to thereby produce the compound represented by formula (8).

The reduction may be performed in the same manner as employed in step (b) or (e). Similar to steps (b) and (e), the reduction is preferably performed through catalytic reduction (hydrogenation in the presence of a catalyst), more preferably through catalytic reduction under basic conditions realized through addition of a base. From the viewpoints of yield and suppression of by-products, $R^4$, $R^5$ and $R^6$ are preferably protected.

Examples of the catalyst employed therein include Pd, Ru, Rh, Pt, Ni and Cu. Of these, Pd and Pt are more preferred. Such a metal may be supported on a carrier such as carbon. Alternatively, PdO, Pd(OH)$_2$, and a metal poisoned by a nitrogen compound (e.g., ethylenediamine), a sulfur compound (e.g., Ph$_2$S) or the like may also be used.

The catalytic reduction (hydrogenation in the presence of a catalyst) may be performed in a solvent such as water, an alcohol such as methanol or ethanol, dimethoxyethane, dioxane, dimethylformamide, dimethylacetamide, THF, DMSO, nitromethane, acetone, ethyl acetate, toluene or acetic acid. Among these solvents, an alcohol, THF, ethyl acetate, and toluene are preferred, with ethyl acetate being more preferred. In one embodiment, the catalyst is used in an amount of 0.01 to 5 parts by mass, preferably 0.1 to 2 parts by mass, with respect to 1 part by mass of the relevant compound. The hydrogen pressure is normal pressure to 10 MPa, preferably normal pressure to 0.5 MPa, more preferably normal pressure. The reaction temperature is 0 to 80° C., preferably 20 to 50° C. The reaction time is 1 to 72 hours, preferably 1 to 24 hours.

Also, the catalytic reduction (hydrogenation in the presence of a catalyst) is preferably performed under basic conditions realized through addition of a base, from the viewpoints of selectivity of reaction and yield of the target product. Examples of the base include inorganic bases such as sodium hydroxide, potassium hydroxide, potassium carbonate, sodium carbonate, sodium hydrogencarbonate, potassium hydrogencarbonate, potassium acetate, potassium t-butoxide, potassium phosphate and aqueous ammonia; and organic bases such as imidazole, trimethylamine, triethylamine, diethylamine, propylamine, tetramethylammonium hydroxide, aniline, N,N-dimethylaniline, dimethylaminopyridine and diazabicycloundecene. From the viewpoint of suppression of by-products, preferred is addition of an inorganic base having a pKa of 8 to 12; such as potassium carbonate, sodium carbonate, sodium hydrogencarbonate, potassium hydrogencarbonate, potassium acetate, potassium phosphate or aqueous ammonia, or addition of an organic base having a pKa of 8 to 12; such as trimethylamine, triethylamine, diethylamine, propylamine, N,N-dimethylaniline or aqueous ammonia. These bases may be used singly or in combination of two or more species. The base is preferably used in an amount 1 to 50 mol with respect to 1 mol of the compound represented by formula (7).

In the catalytic reduction (hydrogenation in the presence of a catalyst) performed in step (j), when an inorganic base such as potassium carbonate is added, the reaction proceeds in a diastereoselective manner, to thereby yield a single diastereomer (8a). When an organic base such as triethylamine is added, a mixture of diastereomers (8a) and (8b) are produced. The diastereomers (8a) and (8b) can be separated from each other through chromatography, to thereby yield single diastereomers (8a) and (8b). The diastereomers (8a) and (8b) may be deprotected through the method employed in step (m), whereby single diastereomers (4a) and (4b) can be formed.

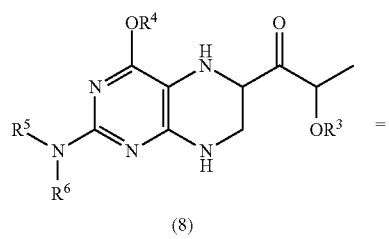

(8)

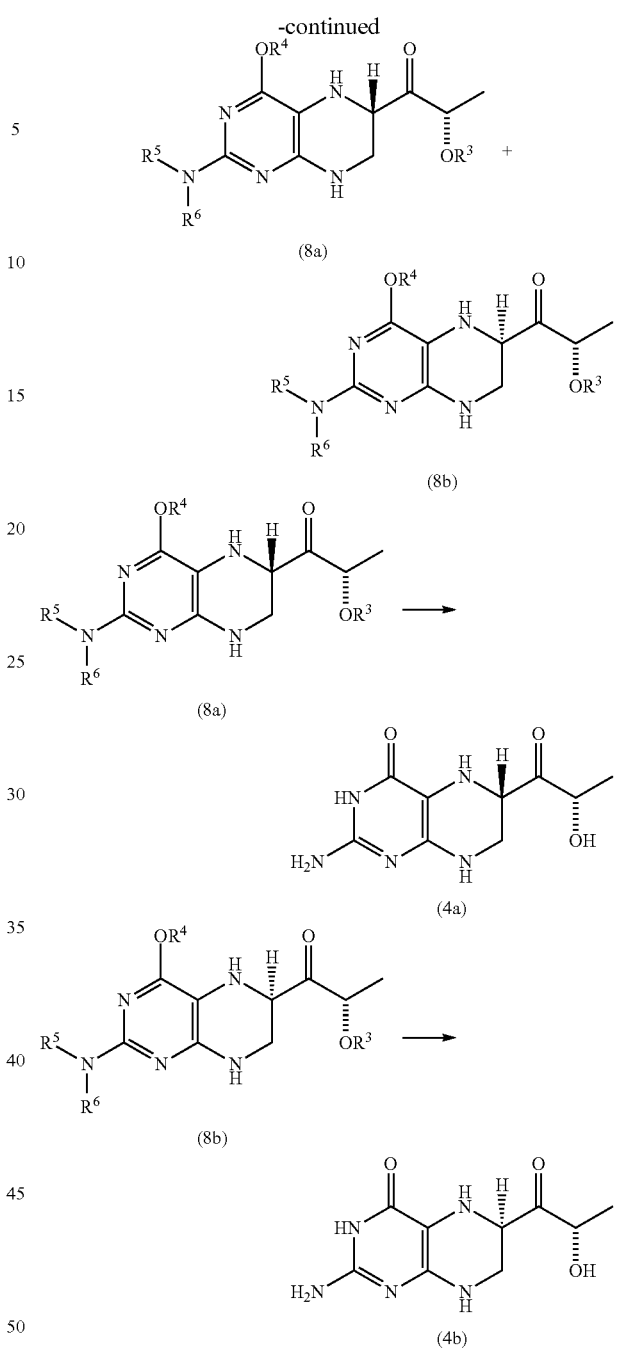

In step (j), preferably, the reaction mixture is acidified immediately after completion of reaction, from the viewpoint of prevention of side reaction.

[Step (k)]

Step (k) is a step of oxidizing the compound represented by formula (8), to thereby form the compound represented by formula (5-1). The reaction is a selective oxidation of 5- and 6-positions of the pterin skeleton.

The oxidation is performed by use of an oxidizing agent or through oxygen oxidation. Examples of the oxidizing agent include a metallic oxidizing agent such as chromic acid or a manganese compound; organic compounds such as DMSO, quinone, acetone, a hypervalent iodine compound and TEMPO; and peracids such as hydrogen peroxide, peracetic acid and perbenzoic acid. Oxygen oxidation is performed by means of air, oxygen, ozone or the like. The oxygen oxidation may be performed in the presence of a catalyst such as Pd, Ru, Rh, Pt, Ni or Cu. Among the oxidation processes, oxidation by use of a peracid or oxygen oxidation is preferred. More preferably, oxygen oxidation by means of air is performed.

In one embodiment of oxygen oxidation (e.g., air oxidation), a solution containing the compound represented by formula (8) is stirred in air for 1 to 72 hours. Oxygen oxidation is preferably performed under neutral or basic conditions.

[Step (i)]

Step (i) is a step of directly reducing the compound represented by formula (7), to thereby produce the compound represented by formula (5-1).

The reduction may be performed in the same manner as employed in step (b) or (e). Similar to steps (b) and (e), the reduction is preferably performed through catalytic reduction (hydrogenation in the presence of a catalyst), more preferably through catalytic reduction under basic conditions realized through addition of a base. From the viewpoints of yield and suppression of by-products, $R^4$, $R^5$ and $R^6$ are preferably protected.

[Step (m)]

Step (m) is a step of deprotecting the compound represented by formula (8), to thereby produce the compound represented by formula (4) (tetrahydrolactoylpterin).

Step (m) may be carried out in the same manner as employed in step (a) or (f).

[Step (l)]

Step (l) is a step of deprotecting the compound represented by formula (5-1, to thereby produce the compound represented by formula (3) (sepiapterin).

Step (l) may be carried out in the same manner as employed in step (a), (f) or (m).

The compound represented by formula (4) can be separated into diastereomers (4a) and (4b) through preferential crystallization. For example, a mixture of (4a) and (4b) is stirred in an aqueous solution (e.g., water or hydrochloric acid) or in a mixture of an aqueous solution (e.g., water or hydrochloric acid) with an alcoholic solvent (e.g., methanol, ethanol or butanol) or an organic solvent (e.g., acetone or acetonitrile), and the mixture is filtered. The diastereomer (4a) can be recovered from the crystals, and the diastereomer (4b) can be recovered from the filtrate.

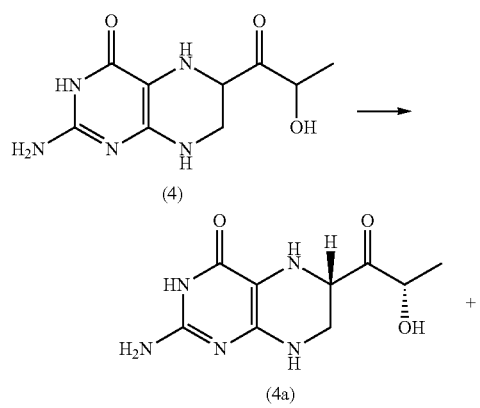

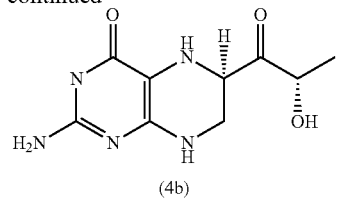

Sepiapterin, lactoylpterin or tetrahydrolactoylpterin may be converted into the corresponding acid addition salt. Examples of the acid to be added include hydrochloric acid, sulfuric acid, nitric acid, phosphoric acid, p-toluenesulfonic acid, methanesulfonic acid and acetic acid. In one procedure of forming such an acid addition salt, sepiapterin, lactoylpterin or tetrahydrolactoylpterin is added to a solvent such as water or alcohol, and an acid is added to the solution.

A desired compound; i.e., sepiapterin, lactoylpterin, tetrahydrolactoylpterin, or a salt thereof may be separated from a reaction mixture by recovering crystals precipitated through filtering. Various chromatographic treatments, recrystallization, and other treatments may be carried out.

EXAMPLES

The present invention will next be described in detail by way of examples.

Referential Example 1

Synthesis of Compound (1)

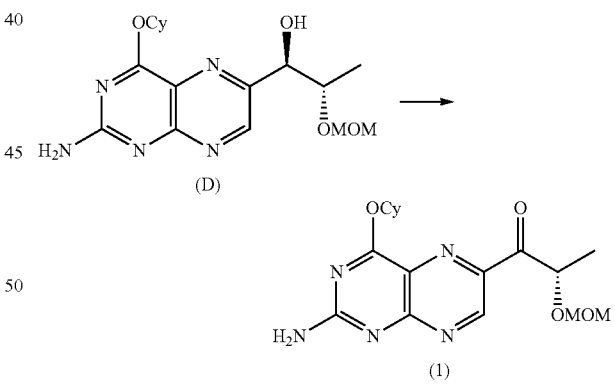

Under argon atmosphere, tetrapropylammonium perruthenate, 4-methylmorpholine N-oxide, and compound (D) were added to acetonitrile in the presence of MS-4A and the mixture was stirred at 60° C. After one hour, the reaction mixture was filtered through Celite™545, and 10% aqueous ammonium chloride solution was added to the filtrate, followed by extraction with ethyl acetate. The extract was dried over magnesium sulfate, concentrated and separated and purified through silica gel column chromatography. The thus-separated product was decanted by use of toluene, to thereby yield compound (1).

Example 1

Synthesis of S-lactoylpterin (2)

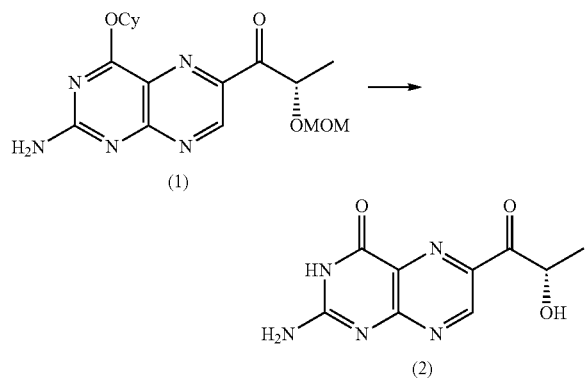

Methanol (50 mL) and 3-mol/L hydrochloric acid (250 mL) were added to 1-(2-amino-4-cyclohexyloxypteridin-6-yl)-2S-methoxymethoxypropan-1-one (compound (1)) (24.7 g, 68.2 mmol), and the mixture was stirred at 50° C. for 3 hours. The pH of the reaction mixture was adjusted with aqueous sodium hydroxide solution to 7. The formed crystals were recovered through filtration and dried under reduced pressure, to thereby yield S-lactoylpterin (15.1 g, 64.2 mmol, yield: 94%). (S-lactoylpterin: (2))

$^1$H NMR (DMSO-$d_6$): δ/ppm=1.32 (d, 3H, J=6.8 Hz), 5.16 (br, 1H), 5.32 (q, 1H, J=6.8 Hz), 9.09 (s, 1H)

Example 2

Synthesis of 1-(2-amino-4-cyclohexyloxypteridin-6-yl)-2S-hydroxypropan-1-one

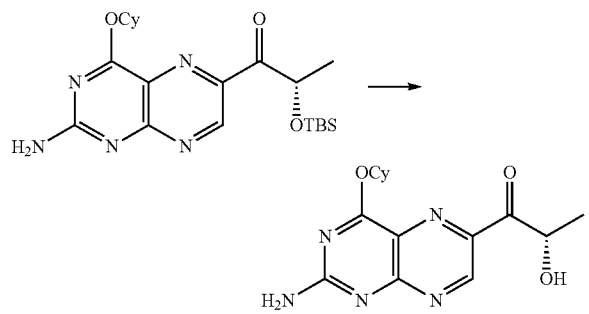

THF (40 mL) and 70% tetrabutylammonium fluoride (6.92 g, 18.5 mmol) were added to 1-(2-amino-4-cyclohexyloxypteridin-6-yl)-2S-t-butyldimethylsilanoxypropan-1-one (compound (1)) (4.0 g, 9.27 mmol), and the mixture was stirred at 10° C. or lower for 2 hours. Water was added to the reaction mixture, and extraction with chloroform was performed. The obtained organic layer was dehydrate and concentrated under reduced pressure. The thus-recovered crude product was purified through flash chromatography, to thereby yield 1-(2-amino-4-cyclohexyloxypteridin-6-yl)-2S-hydroxypropan-1-one (2.09 g, 6.59 mmol, yield: 71%).

$^1$H NMR (DMSO-$d_6$): δ/ppm=1.38 (d, 3H, J=6.6 Hz), 1.37-1.79 (m, 8H), 1.98-1.99 (m, 2H), 5.20 (d, 1H, J=6.3 Hz), 5.34 (d.q., 1H, J=6.6 Hz), 5.29-5.37 (m, 1H), 7.68 (br, 1H), 7.82 (br, 1H), 9.22 (s, 1H)

Example 3

Synthesis of S-lactoylpterin hydrochloride

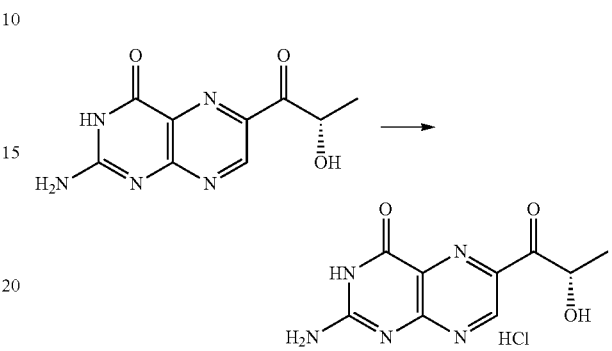

6-mol/L Hydrochloric acid (1.25 mL) and ethanol (10 mL) were added to S-lactoylpterin (500 mg, 2.13 mmol), and the mixture was stirred 30 minutes. The formed crystals were recovered through filtration and dried under reduced pressure, to thereby yield S-lactoylpterin hydrochloride (465 mg, 1.71 mmol, yield: 80%).
(S-lactoylpterin hydrochloride)

$^1$H NMR (DMSO-$d_6$): δ/ppm=1.34 (d, 3H, J=6.9 Hz), 3.91 (br, 3H), 5.34 (q, 1H, J=6.9 Hz), 9.12 (s, 1H)

Example 4

Synthesis of 2-amino-6-(2S-hydroxypropionyl)-7,8-dihydro-3H-pteridin-4-one (S-sepiapterin)

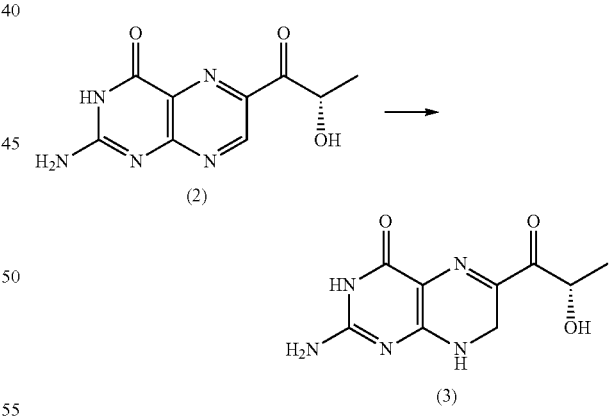

To S-lactoylpterin (500 mg, 2.13 mol), methanol (125 mL), triethylamine (2.08 mL, 14.9 mmol), and 8.4% Pd/C (Ph$_2$S) (50% water content) (250 mg) were added, and the mixture was subjected to hydrogenation at an external temperature of 40° C. for 3 hours. After completion of reaction, the reaction mixture was stirred at room temperature for 1 hour in air, and the catalyst was filtered off from the reaction mixture. The filtrate was concentrated under reduced pressure, and the thus-recovered crude product was separated and purified through flash chromatography, to thereby yield S-sepiapterin (296 mg, 1.25 mmol, yield: 59%).

(S-sepiapterin: (3))

$^1$H NMR (DMSO-d$_6$): δ/ppm=1.21 (d, 3H, J=6.6 Hz), 4.11 (s, 2H), 4.89 (d, 1H, J=6.6 Hz), 5.10 (quin., 1H, J=6.6 Hz), 6.81 (br-s, 2H), 7.51 (s, 1H), 10.26 (s, 1H)

Example 5

Saturated aqueous sodium bicarbonate solution (2 mL) and sodium dithionite (76 mg, 0.44 mmol) were added to S-lactoylpterin (20 mg, 0.085 mmol), and the mixture was stirred at room temperature for 2 hours, to thereby yield S-sepiapterin as a mixture.

Example 6

The procedure of Example 5 was repeated, except that aqueous sodium borate solution was added to S-lactoylpterin (20 mg, 0.085 mmol) instead of saturated aqueous sodium bicarbonate solution, to thereby yield S-sepiapterin as a mixture.

Example 7

Synthesis of S-sepiapterin hydrochloride

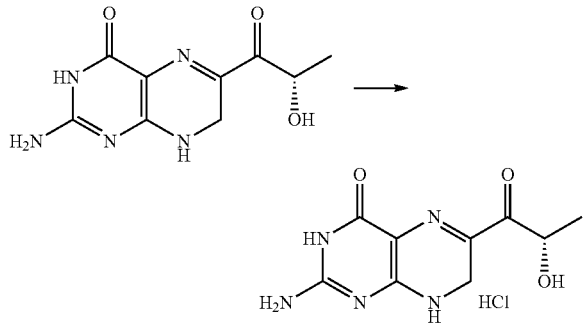

6-mol/L Hydrochloric acid (2.5 mL) and ethanol (5.0 mL) were added to S-sepiapterin (620 mg, 2.61 mmol), and the mixture was stirred at 0° C. for 30 minutes. The formed crystals were recovered through filtration and dried under reduced pressure, to thereby yield S-sepiapterin hydrochloride (650 mg, 2.38 mmol, yield: 91%).

(S-sepiapterin hydrochloride)

$^1$H NMR (DMSO-d$^6$): δ/ppm=1.22 (d, 3H, J=6.9 Hz), 4.14 (s, 2H), 4.89 (d, 1H, J=6.6 Hz), 5.11 (q, 1H, J=6.9 Hz), 7.40 (br-s, 4H), 7.80 (br-s, 1H)

Example 8

Synthesis of 2-amino-6-(2S-hydroxypropionyl)-5,6,7,8-tetrahydro-3H-pteridin-4-one (S-tetrahydrolactoylpterin) dihydrochloride

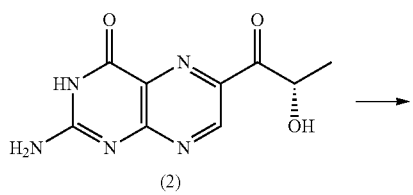

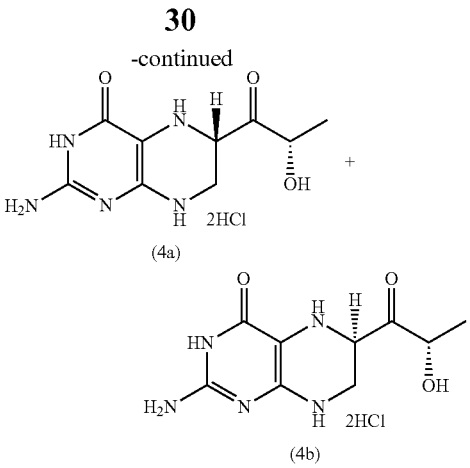

To S-lactoylpterin (1.00 g, 4.25 mmol), methanol (50 mL), 6-mol/L hydrochloric acid (5 mL) and borane-pyridine complex (593 mg, 6.38 mmol) were added, and the mixture was stirred at an external temperature of 0° C. for 1 hour. After completion of reaction, acetone (5 mL) was added thereto, and the mixture was concentrated under reduced pressure. Subsequently, the mixture was subjected to azeotropic dehydration with ethanol. Ethanol was further added, and the thus-formed crystals were recovered through filtration and dried under reduced pressure, to thereby yield a mixture of S-tetrahydrolactoylpterin dihydrochlorides (4a) and (4b) (1.12 g, 3.59 mmol, yield: 85%).

(6S—S-tetrahydrolactoylpterin dihydrochloride: (4a))

$^1$H NMR (DMSO-d$^6$): δ/ppm=1.24 (d, 3H, J=6.9 Hz), 3.45 (dd, 1H, J=7.2, 13.5 Hz), 3.87 (dd, 1H, J=3.3, 13.5 Hz), 4.34 (q, 1H, J=6.9 Hz), 4.53 (dd, 1H, J=3.3, 7.2 Hz), 7.03 (br-s, 4H), 7.67 (br-s, 1H)

(6R—S-tetrahydrolactoylpterin dihydrochloride: (4b))

$^1$H NMR (DMSO-d$^6$): δ/ppm=1.24 (d, 3H, J=6.9 Hz), 3.45 (dd, 1H, J=6.9, 13.5 Hz), 3.91 (dd, 1H, J=3.3, 13.5 Hz), 4.31 (q, 1H, J=6.6 Hz), 4.55 (dd, 1H, J=3.3, 6.9 Hz), 7.12 (br-s, 3H), 7.71 (br-s, 2H)

Example 9

To S-lactoylpterin (3.00 g, 12.8 mmol), methanol (150 mL), 6-mol/L hydrochloric acid (15 mL) and borane-pyridine complex (1.78 g, 19.1 mmol) were added, and the mixture was stirred at an external temperature of 0° C. for 1 hour. After completion of reaction, concentrated hydrochloric acid (45 mL) was added thereto, and the mixture was stirred overnight at the same temperature. The formed crystals were recovered through filtration and dried under reduced pressure, to thereby yield 6S—S-tetrahydrolactoylpterin dihydrochloride (4a) (1.63 g, 5.2 mmol, yield: 41%). Also, the filtrate was concentrated under reduced pressure and dehydrated through co-boiling with ethanol. Ethanol was further added, and the thus-formed crystals were recovered through filtration and dried under reduced pressure, to thereby yield 6R—S-tetrahydrolactoylpterin dihydrochloride (4b) (1.38 g, 4.4 mmol, yield: 35%). The compounds produced were found to have the same spectral data as those obtained in Example 8.

Example 10

To S-lactoylpterin (100 mg, 0.43 mmol), methanol (5 mL), 6-mol/L hydrochloric acid (0.5 mL) and boran-pyridine complex (59 mg, 0.64 mmol) were added, and the mixture was stirred over night at an external temperature of 0° C. The formed crystals were recovered through filtration and dried under reduced pressure, to thereby yield 6S—S-tetrahydrolactoylpterin dihydrochloride (4a) (46 mg, 0.15 mmol, yield: 35%). The compound produced was found to have the same spectral data as those obtained in Example 8.

Example 11

To S-lactoylpterin (200 mg, 0.85 mol), methanol (50 mL), diethylamine (0.62 mL, 5.95 mmol) and 8.4% Pd/C (Ph₂S) (50% water content) (100 mg) were added, and the mixture was subjected to hydrogenation at an external temperature of 40° C. for 2.5 hours. After completion of reaction, concentrated hydrochloric acid was added to the reaction mixture, and the catalyst was filtered off from the reaction mixture. The obtained liquid was concentrated under reduced pressure and subjected to azeotropic dehydration with ethanol. Ethanol was further added, and the thus-formed crystals were recovered through filtration and dried under reduced pressure, to thereby yield a mixture of S-tetrahydrolactoylpterin dihydrochlorides (4a) and (4b) (122 mg, 0.39 mmol, yield: 46%). The compounds produced were found to have the same spectral data as those obtained in Example 8.

Example 12

Synthesis of 2-amino-6-(2S-hydroxypropionyl)-5,6,7,8-tetrahydro-3H-pteridin-4-one (S-tetrahydrolactoylpterin) ditoluenesulfonate

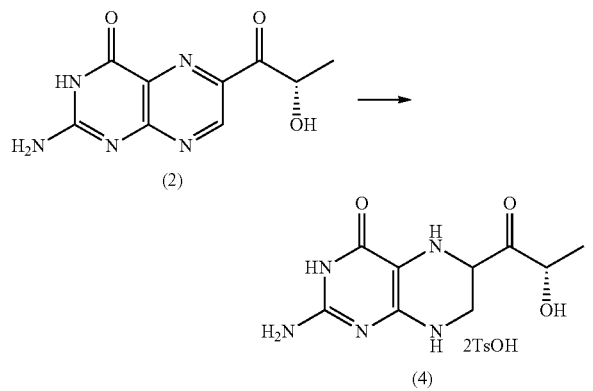

To S-lactoylpterin (100 mg, 0.43 mmol), methanol (5 mL), water (0.5 mL), p-toluenesulfonic acid monohydrate (566 mg, 2.98 mmol) and borane-pyridine complex (59 mg, 0.64 mmol) were added, and the mixture was stirred at an external temperature of 0° C. for 1 hour. After completion of reaction, acetone (0.5 mL) was added thereto, and the mixture was concentrated under reduced pressure. Subsequently, the mixture was subjected to azeotropic dehydration with ethanol. Acetone was further added, and the thus-formed crystals were recovered through filtration and dried under reduced pressure, to thereby yield S-tetrahydrolactoylpterin ditoluenesulfonate (158 mg, 0.27 mmol, yield: 63%).
(S-tetrahydrolactoylpterin ditoluenesulfonate)
¹H NMR (DMSO-d⁶): δ/ppm=1.25 (d, 3H, J=7.2 Hz), 2.29 (S, 6H), 3.35 (dd, 1H, J=7.5, 13.5 Hz), 3.84 (dd, 1H, J=3.0, 13.5 Hz), 4.35 (q, 1H, J=6.9 Hz), 4.49 (dd, 1H, J=3.0, 7.5 Hz), 6.72 (br-s, 2H), 7.13 (d, 4H, J=8.1 Hz), 7.49 (d, 4H, J=8.1 Hz), 7.62 (br-s, 1H), 10.66 (br-s, 1H) ¹H NMR (DMSO-d⁶): δ/ppm=1.25 (d, 3H, J=7.2 Hz), 2.29 (S, 6H), 3.33 (dd, 1H, J=7.5, 13.5 Hz), 3.84 (dd, 1H, J=3.0, 13.5 Hz), 4.32 (q, 1H, J=6.9 Hz), 4.49 (dd, 1H, J=3.0, 7.5 Hz), 6.72 (br-s, 2H), 7.13 (d, 4H, J=8.1 Hz), 7.49 (d, 4H, J=8.1 Hz), 7.62 (br-s, 1H), 10.66 (br-s, 1H)

Example 13

Synthesis of 2-amino-6-(2S-hydroxypropionyl)-7,8-dihydro-3H-pteridin-4-one (S-sepiapterin)

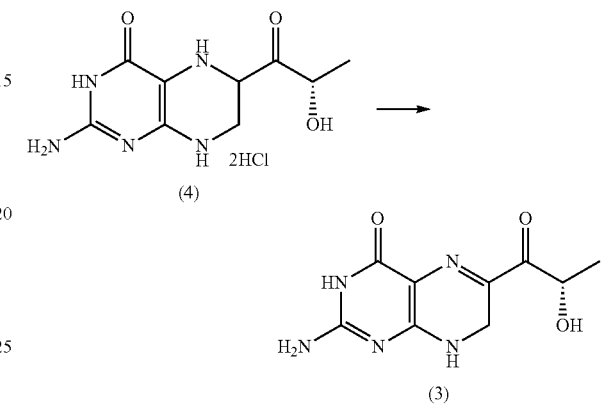

Water (6 mL) and ethanol (6 mL) were added to S-tetrahydrolactoylpterin dihydrochloride (1.00 g, 3.20 mmol), and 30% aqueous hydrogen peroxide solution (363 mg, 3.20 mmol) was added to the mixture at an external temperature of −10° C. The resultant mixture was stirred at the same temperature for 2 hours, and then aqueous sodium sulfite solution was added to the reaction mixture. The thus-formed crystals were recovered through filtration and dried under reduced pressure, to thereby yield S-sepiapterin (676 mg, 2.85 mmol, yield: 89%). The obtained compound was found to have the same spectral data as those obtained in Example 4.

Example 14

The procedure of Example 13 was repeated, except that 36% peracetic acid (68 mg, 0.32 mmol) was added to S-tetrahydrolactoylpterin dihydrochloride (100 mg, 0.32 mmol) instead of 30% aqueous hydrogen peroxide, to thereby yield S-sepiapterin (46 mg, 0.19 mmol, yield: 61%). The obtained compound was found to have the same spectral data as those obtained in Example 4.

Example 15

The procedure of Example 13 was repeated, except that m-CPBA (85 mg, content: 65%, 0.32 mmol) was added to S-tetrahydrolactoylpterin dihydrochloride (100 mg, 0.32 mmol) instead of 30% aqueous hydrogen peroxide, to thereby yield S-sepiapterin (35 mg, 0.15 mmol, yield: 46%). The obtained compound was found to have the same spectral data as those obtained in Example 4.

Example 16

Methanol (20 mL) and triethylamine (0.89 mL, 6.40 mmol) were added to S-tetrahydrolactoylpterin dihydrochloride (200 mg, 0.64 mmol), and the mixture was stirred in air at room temperature for 1 hour. The reaction mixture was concentrated under reduced pressure, and water was added thereto. The thus-formed crystals were recovered through filtration and dried under reduced pressure, to thereby yield S-sepiapterin (105 mg, 0.44 mmol, yield: 69%). The obtained compound was found to have the same spectral data as those obtained in Example 4.

Example 17

Methanol (20 mL) was added to S-tetrahydrolactoylpterin dihydrochloride (200 mg, 0.64 mmol), and the mixture was neutralized with 8-mol/L aqueous sodium hydroxide solution (0.16 mL, 1.28 mmol). The neutralized product was stirred in air at room temperature for 1 hour. The reaction mixture was concentrated under reduced pressure, and water was added thereto. The thus-formed crystals were recovered through filtration and dried under reduced pressure, to thereby yield S-sepiapterin (87 mg, 0.37 mmol, yield: 58%). The obtained compound was found to have the same spectral data as those obtained in Example 4.

Example 18

Synthesis of 1-(2-amino-4-cyclohexyloxy-7,8-dihydropteridin-6-yl)-2S-methoxymethoxypropan-1-one

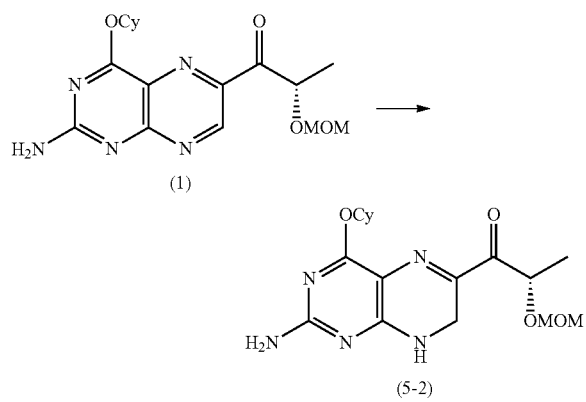

To 1-(2-amino-4-cyclohexyloxypteridin-6-yl)-2S-methoxymethoxypropan-1-one (1.00 g, 2.77 mmol), ethyl acetate (60 mL), 10% Pd—C (500 mg), and potassium carbonate (3.82 g, 27.6 mmol) were added, and the mixture was subjected to hydrogenation at an external temperature of 50° C. for 3 hours. After removal of the catalyst through filtration, the reaction mixture was concentrated under reduced pressure. The thus-recovered crude product was separated and purified through flash chromatography, to thereby yield 1-(2-amino-4-cyclohexyloxy-7,8-dihydropteridin-6-yl)-2S-methoxymethoxypropan-1-one (257 mg, 0.71 mmol, yield: 26%).

$^1$H NMR (CDCl$_3$): δ/ppm=1.33-1.47 (m, 3H), 1.44 (d, 3H, J=6.9 Hz), 1.54-1.63 (m, 3H), 1.79 (m, 2H), 1.91 (m, 2H), 3.37 (s, 3H), 4.36 (d, 1H, J=15.6), 4.43 (d, 1H, J=15.6), 4.71 (d, 1H, J=6.6 Hz), 4.74 (d, 1H, J=6.6 Hz), 4.90 (br-s, 2H), 5.00 (br-s, 1H), 5.05-5.11 (m, 1H), 5.34 (q, 1H, J=6.9 Hz)

Example 19

Synthesis of 1-(2-amino-4-cyclohexyloxy-7,8-dihydropteridin-6-yl)-2S-methoxyethoxymethoxypropan-1-one

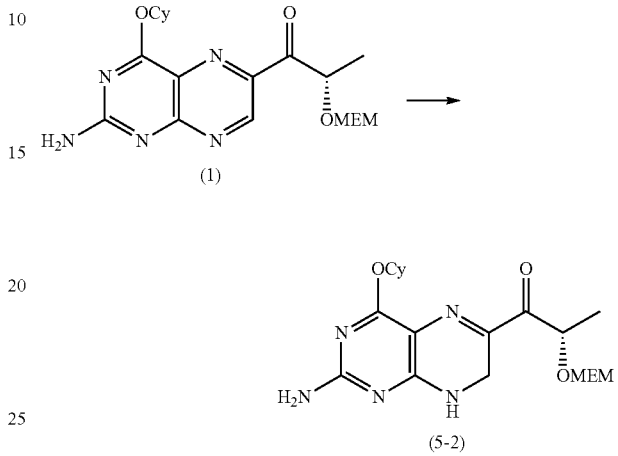

Water (2 mL) was added to weighed ascorbic acid (100 mg, 0.56 mmol), and the obtained solution was neutralized with 1-mol/L aqueous sodium hydroxide solution. Then, 1-(2-amino-4-cyclohexyloxypteridin-6-yl)-2S-methoxyethoxymethoxypropan-1-one (20 mg, 0.054 mmol) dissolved in methanol (2 mL) was added to the neutral solution. Na$_2$S$_2$O$_4$ (80 mg, 0.46 mmol) was added thereto, and the mixture was stirred at room temperature for 1 hour. Water was added to the reaction mixture, and the mixture was subjected to extraction with ethyl acetate. The thus-obtained organic phase was dehydrated and concentrated under reduced pressure. The concentrate was separated and purified through silica gel chromatography, to thereby yield 1-(2-amino-4-cyclohexyloxy-7,8-dihydropteridin-6-yl)-2S-methoxyethoxymethoxypropan-1-one (4.4 mg, 0.011 mmol, yield: 20%).

$^1$H NMR (CDCl$_3$): δ/ppm=1.13 (m, 1H), 1.44 (d, 3H, J=6.8 Hz), 1.63 (m, 1H), 1.80 (m, 2H), 1.93 (m, 2H), 2.06 (m, 2H), 3.37 (s, 3H), 3.52 (m, 2H), 3.70 (t, J=4.6 Hz, 2H), 4.40 (m, 2H), 4.81 (m, 2H), 5.11 (t.t, J=3.9, 8.5 Hz, 1H), 5.35 (q, J=6.8 Hz, 1H)

Example 20

Synthesis of S-sepiapterin (3)

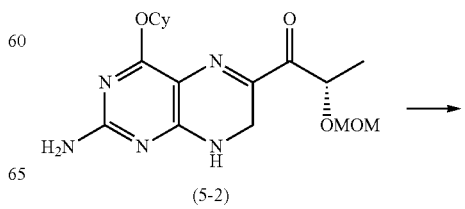

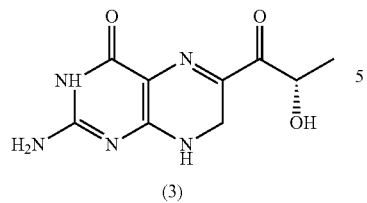

(3)

Concentrated hydrochloric acid (0.1 mL) was added to 1-(2-amino-4-cyclohexyloxy-7,8-dihydropteridin-6-yl)-2S-methoxymethoxypropan-1-one (compound (5-2)) (10 mg), and the mixture was heated. The reaction mixture was diluted with water, and the diluted product was neutralized with aqueous sodium hydroxide solution so as to adjust the pH thereof to 6 to 7. The precipitated crystals were removed through filtration. The filtrate was concentrated under reduced pressure, to thereby yield S-sepiapterin as a mixture. The thus-produced compound was found to have the same spectral data as those obtained in Example 4.

Example 21

Synthesis of S-sepiapterin (3)

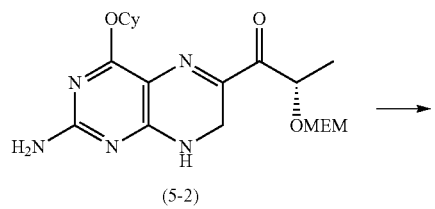

(5-2)

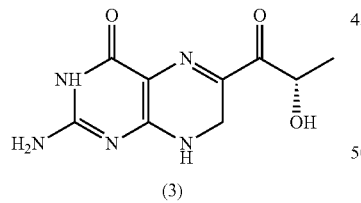

(3)

1-(2-Amino-4-cyclohexyloxy-7,8-dihydropteridin-6-yl)-2S-methoxyethoxymethoxypropan-1-one (4.0 mg, 9.8 μmol) and ascorbic acid (3.0 mg) were added to methanol (2 mL), and 3-mol/L hydrochloric acid (2 mL) was added to the mixture. The resultant mixture was stirred at 50° C. for 6 hours under light-shielded conditions. Then, the mixture was neutralized with 28% aqueous ammonia to a pH of 7. The neutralized product was washed with ethyl acetate and purified through Florisil column chromatography, to thereby yield S-sepiapterin (2.0 mg, 8.4 μmol, yield: 86%). The retention time and UV peak profile in HPLC coincided with those of an S-sepiapterin standard sample.

Example 22

Synthesis of 2-amino-6-[2S-(tert-butyldimethylsilanyloxy)-propionyl]-3H-pteridin-4-one (6)

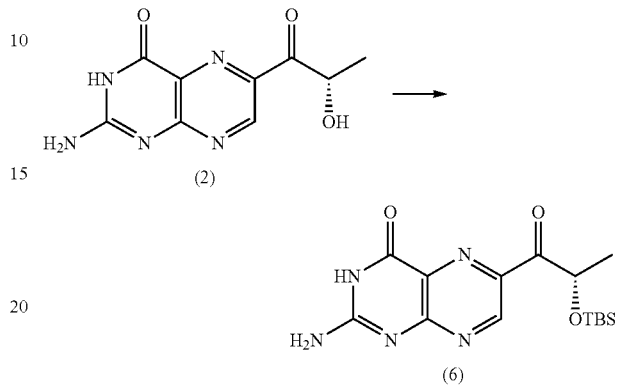

To S-lactoylpterin (3.00 g, 12.8 mmol), DMF (30 mL), imidazole (2.61 g, 38.3 mmol) and TBSCl (3.84 g, 25.5 mmol) were added, and the mixture was stirred for 1 hour under ice-cooling conditions. Water was added to the reaction mixture, and the thus-formed crystals were recovered through filtration and dried under reduced pressure, to thereby yield 2-amino-6-[2S-(tert-butyldimethylsilanyloxy)-propionyl]-3H-pteridin-4-one (6) (3.91 g, 11.2 mmol, yield: 88%).

$^1$H NMR (DMSO-d$^6$): δ/ppm=0.01 (s, 3H), 0.06 (s, 3H), 0.83 (s, 9H), 1.36 (d, 3H, J=6.9 Hz), 5.55 (q, 1H, J=6.9 Hz), 9.10 (s, 1H), 11.73 (br-s, 1H)

Example 23

Synthesis of 2-amino-6-[2S-(triisopropylsilanyl)-propionyl]-3H-pteridin-4-one (6))

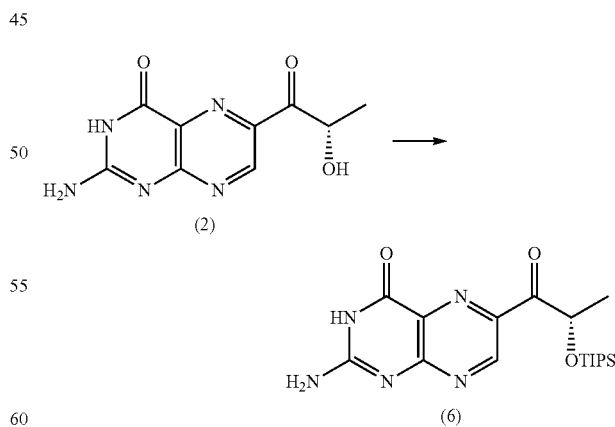

The procedure of Example 22 was repeated, except that TIPSCl was added to S-lactoylpterin (300 mg, 1.28 mmol) instead of TBSCl, to thereby yield 2-amino-6-[2S-(triisopropylsilanyl)-propionyl]-3H-pteridin-4-one (6) (339 mg, 0.87 mmol, yield: 68%).

¹H NMR (DMSO-d⁶): δ/ppm=0.89-1.15 (m, 21H), 1.40 (d, 3H, J=6.9 Hz), 5.71 (q, 1H, J=6.9 Hz), 9.13 (s, 1H), 11.74 (br-s, 1H)

Example 24

Synthesis of 2-amino-6-[2S-(tert-butyldiphenylsilanyl)-propionyl]-3H-pteridin-4-one (6)

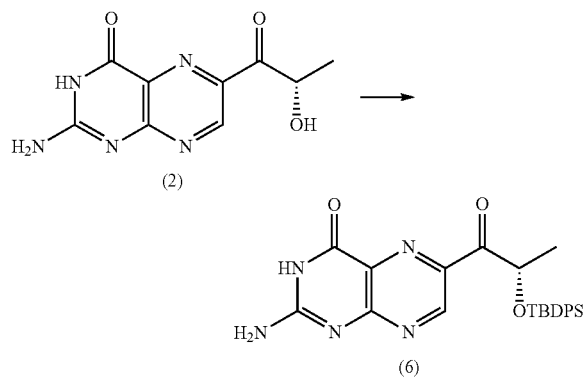

The procedure of Example 22 was repeated, except that TBDPSCl was added to S-lactoylpterin (300 mg, 1.28 mmol) instead of TBSCl, to thereby yield 2-amino-6-[2S-(triisopropylsilany)-propionyl]-3H-pteridin-4-one (6) (498 mg, 1.05 mmol, yield: 82%).

¹H NMR (DMSO-d⁶): δ/ppm=1.03 (s, 9H), 1.38 (d, 3H, J=6.9 Hz), 5.71 (q, 1H, J=6.9 Hz), 7.23-7.33 (m, 3H), 7.37-7.45 (m, 3H), 7.50-7.59 (m, 2H), 7.61-7.71 (m, 2H), 8.96 (s, 1H), 11.67 (br-s, 1H)

Example 25

Synthesis of 1-[4-tert-butoxycarbonyl-2-(N,N-di-tert-butoxycarbonyl)aminopteridin-6-yl]-2S-tert-butyldimethylsilanyloxypropan-1-one (7)

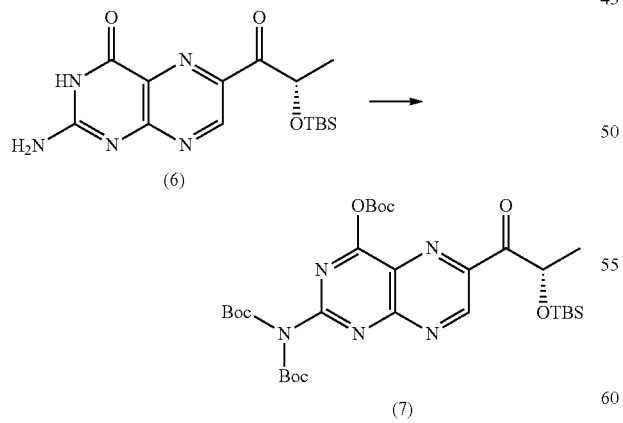

To 2-amino-6-[2S-(tert-butyldimethylsilanyloxy)-propionyl]-3H-pteridin-4-one (1.50 g, 4.29 mmol), ethyl acetate (75 mL), di-tert-butyl dicarbonate (4.68 g, 21.4 mmol) and N,N-dimethylaminopyridine (52 mg, 0.43 mmol) were added, and the mixture was refluxed with heating for 1 hour. The reaction mixture was washed with water. The recovered organic layer was dehydrated and concentrated under reduced pressure, to thereby yield 2-(N,N-di-tert-butylcarbonyl)-amino-6-[2S-(tert-butyldimethylsilanyloxy)-propionly]-3H-pteridin-4-one (7) (2.18 g, 3.35 mmol, yield: 78%).

¹H NMR (DMSO-d⁶): δ/ppm=0.01 (s, 3H), 0.08 (s, 3H), 0.75 (s, 9H), 1.40 (d, 3H, J=6.6 Hz), 1.48 (s, 18H), 1.71 (s, 9H), 5.59 (q, 1H, J=6.6 Hz), 9.53 (s, 1H)

Example 26

Synthesis of 1-[4-tert-butoxycarbonyl-2-(N,N-di-tert-butoxycarbonyl)aminopteridin-6-yl]-2S-tert-butoxycarbonyloxypropan-1-one (7)

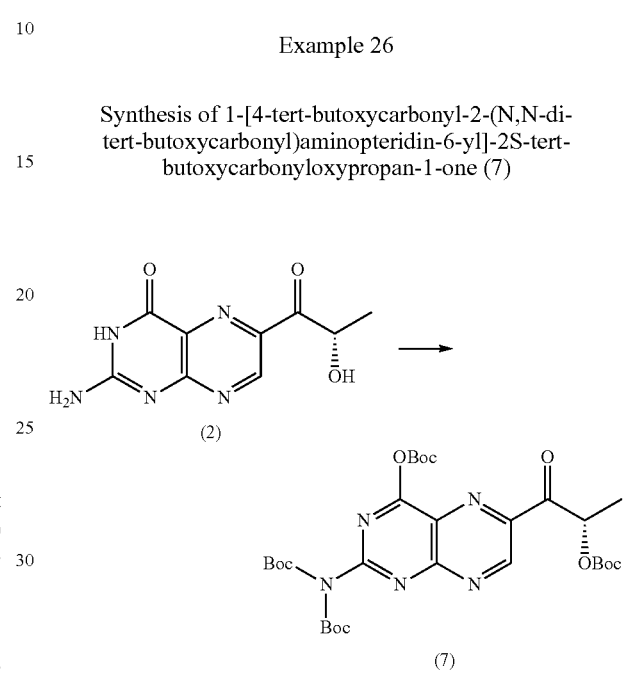

To S-lactoylpterin (1.00 g, 4.25 mmol), THF (50 mL), di-tert-butyl dicarbonate (4.64 g, 21.3 mmol) and N,N-dimethylaminopyridine (30 mg, 0.25 mmol) were added, and the mixture was refluxed with heating for 3 hours. The reaction mixture was concentrated under reduced pressure, and the obtained crude product was separated and purified through flash chromatography, to thereby yield 1-[4-tert-butoxycarbonyl-2-(N,N-di-tert-butoxycarbonyl)aminopteridin-6-yl]-2S-tert-butoxycarbonyloxypropan-1-one (7) (0.30 g, 0.47 mmol, yield: 11%).

¹H NMR (CDCl₃): δ/ppm=1.26 (s, 9H), 1.27 (d, 3H, J=7.2 Hz), 1.45 (s, 18H), 1.71 (s, 9H), 6.11 (q, 1H, J=7.2 Hz), 6.73 (s, 1H)

Example 27

Synthesis of 1-[4-cyclohexyloxy-2-(N,N-di-tert-butoxycarbonyl)aminopteridin-6-yl]-2S-methoxymethoxypropan-1-one

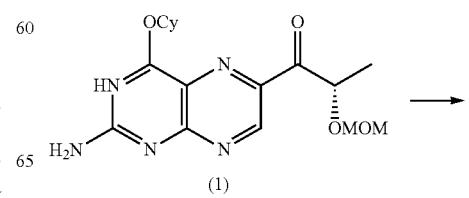

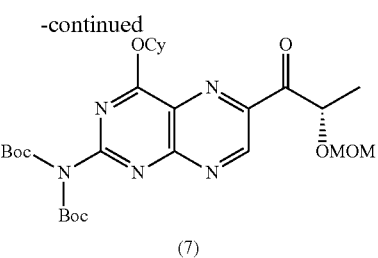

(7)

To 1-(2-amino-4-cyclohexyloxypteridin-6-yl)-2S-methoxymethoxypropan-1-one (1.00 g, 2.76 mmol), THF (20 mL), di-tert-butyl dicarbonate (1.27 g, 5.82 mmol) and N,N-dimethylaminopyridine (3.4 mg, 0.03 mmol) were added, and the mixture was refluxed with heating for 1 hour. The reaction mixture was concentrated under reduced pressure, to thereby yield 1-[4-cyclohexyloxy-2-(N,N-di-tert-butylcarbonyl)aminopteridin-6-yl]-2S-methoxymethoxypropan-1-one (7) (1.55 g, 2.76 mmol, yield: 100%).

$^1$H NMR (DMSO-d$^6$): δ/ppm=1.45-1.88 (m, 8H), 1.53 (s, 18H), 1.58 (d, 3H, J=6.9 Hz), 2.10-2.14 (m, 2H), 3.38 (s, 3H), 4.78 (d, 1H, J=6.9 Hz), 4.84 (d, 1H, J=6.9 Hz), 5.36-5.45 (m, 1H), 5.55 (q, 1H, J=6.9 Hz), 9.65 (s, 1H)

Example 28

Synthesis of 1-[4-tert-butoxycarbonyl-2-(N,N-di-tert-butoxycarbonyl)amino-7,8-dihydropteridin-6-yl]-2S-tert-butyldimethylsilanyloxypropan-1-one

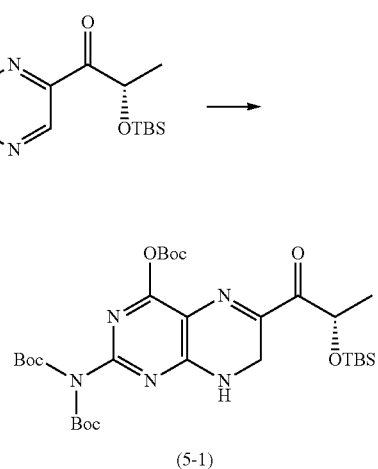

(7)

(5-1)

To 1-[4-tert-butoxycarbonyl-2-(N,N-di-tert-butoxycarbonyl)aminopteridin-6-yl]-2S-tert-butyldimethylsilanyloxypropan-1-one (1.31 g, 2.02 mmol), ethyl acetate (130 mL), 10% Pd—C (655 mg) and potassium carbonate (2.78 g, 20.1 mmol) were added, and the mixture was subjected to hydrogenation at an external temperature of 50° C. and ambient pressure (H$_2$ balloon) for 1 hour. After removal of the catalyst through filtration, the reaction mixture was stirred overnight at room temperature in air and then concentrated under reduced pressure. The thus-recovered crude product was separated and purified through flash chromatography, to thereby yield 1-[4-tert-butoxycarbonyl-2-(N,N-di-tert-butoxycarbonyl)amino-7,8-dihydropteridin-6-yl]-2S-tert-butyldimethylsilanyloxypropan-1-one (684 mg, 1.05 mmol, yield: 66%).

$^1$H NMR (DMSO-d$^6$): δ/ppm=0.01 (s, 3H), 0.07 (s, 3H), 0.82 (s, 9H), 1.24 (d, 3H, J=6.6 Hz), 1.42 (s, 18H), 1.53 (s, 9H), 4.23 (d, 1H, J=16.5 Hz), 4.32 (d, 1H, J=16.5 Hz), 5.39 (q, 1H, J=6.6 Hz), 7.92 (s, 1H)

Example 29

Synthesis of 2-amino-6S-(2S-hydroxypropionyl)-5,6,7,8-tetrahydro-3H-pteridin-4-one(6S—S-tetrahydrolactoylpterin) dihydrochloride

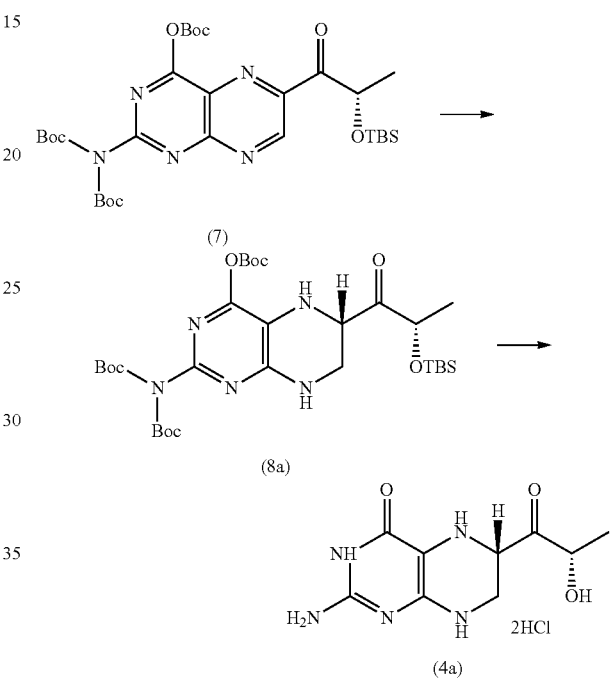

(7)

(8a)

(4a)

To 1-[4-tert-butoxycarbonyl-2-(N,N-di-tert-butoxycarbonyl)aminopteridin-6-yl]-2S-tert-butyldimethylsilanyloxypropan-1-one (4.92 g, 7.57 mmol), ethyl acetate (250 mL), 10% Pd—C (2.46 g) and K$_2$CO$_3$ (10.5 g, 76.0 mmol) were added, and the mixture was subjected to hydrogenation at an external temperature of 50° C. and ambient pressure (H$_2$ balloon) for 1 hour. After removal of the catalyst through filtration, the reaction mixture was concentrated under reduced pressure. Concentrated hydrochloric acid (49 mL) was added to the mixture, and the resultant mixture was concentrated under reduced pressure. Ethanol was added to the concentrate, and the formed crystals were recovered and dried under reduced pressure, to thereby yield 6S—S-tetrahydrolactoylpterin dihydrochloride (4a) (1.79 g, 5.73 mmol, yield: 76%). The thus-produced compound was found to have the same spectral data as those obtained in Example 8.

Example 30

The procedure of Example 29 was repeated, except that 10% Pd/C (100 mg) was added to 1-[4-tert-butoxycarbonyl-2-(N,N-di-tert-butoxycarbonyl)aminopteridin-6-yl]-2S-tert-butyldimethylsilanyloxypropan-1-one (500 mg, 0.77 mmol), to thereby yield 6S—S-tetrahydrolactoylpterin dihydrochloride (4a) (164 mg, 0.53 mmol, yield: 68%). The thus-produced compound was found to have the same spectral data as those obtained in Example 8.

Example 31

Synthesis of 1-[4-tert-butoxycarbonyl-2-(N,N-di-tert-butoxycarbonyl)amino-5,6,7,8-tetrahydropteridin-6-yl]-2S-tert-butyldimethylsilanyloxypropan-1-one)

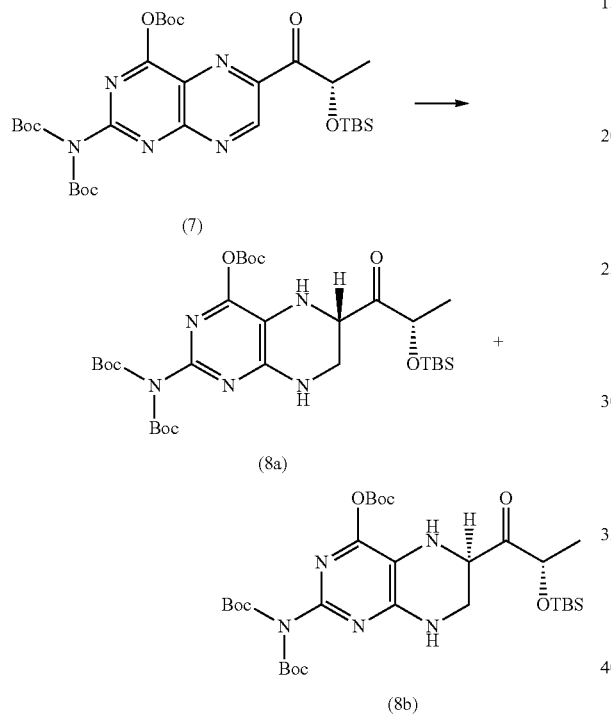

To 1-[4-tert-butoxycarbonyl-2-(N,N-di-tert-butoxycarbonyl)aminopteridin-6-yl]-2S-tert-butyldimethylsilanyloxypropan-1-one (100 mg, 0.15 mmol), ethyl acetate (10 mL), 10% Pd—C (20 mg) and triethylamine (156 mg, 1.54 mmol) were added, and the mixture was subjected to hydrogenation at an external temperature of 50° C. and ambient pressure ($H_2$ balloon) for 1 hour. After removal of the catalyst through filtration, the reaction mixture was concentrated under reduced pressure. The obtained crude product was purified through flash chromatography, to thereby yield 1-[4-tert-butoxycarbonyl-2-(N,N-di-tert-butoxycarbonyl)amino-5,6,7,8-tetrahydropteridin-6 S-yl]-2S-tert-butyldimethylsilanyloxypropan-1-one (8a) (30 mg, 0.045 mmol, yield: 30%) and 1-[4-tert-butoxycarbonyl-2-(N,N-di-tert-butoxycarbonyl)amino-5,6,7,8-tetrahydropteridin-6R-yl]-2 S-tert-butyldimethylsilanyloxypropan-1-one (8b) (30 mg, 0.045 mmol, yield: 30%).

(8a)

$^1$H NMR (DMSO-d$^6$): δ/ppm=0.08 (s, 3H), 0.09 (s, 3H), 0.89 (s, 9H), 1.21 (d, 3H, J=6.6 Hz), 1.37 (s, 18H), 1.49 (s, 9H), 3.56-3.67 (m, 2H), 4.39 (m, 1H), 4.42 (q, 1H, J=6.6 Hz), 4.79 (s, 1H), 7.00 (s, 1H)

(8b)

$^1$H NMR (DMSO-d$^6$): δ/ppm=0.08 (s, 3H), 0.09 (s, 3H), 0.89 (s, 9H), 1.23 (d, 3H, J=6.6 Hz), 1.37 (s, 18H), 1.49 (s, 9H), 3.40-3.53 (m, 2H), 4.35 (m, 1H), 4.44 (q, 1H, J=6.6 Hz), 4.93 (s, 1H), 7.09 (s, 1H)

Example 32

Synthesis of 1-[4-cyclohexyloxy-2-(N,N-di-tert-butoxycarbonyl)amino-5,6,7,8-tetrahydropteridin-6-yl]-2S-methoxymethoxypropan-1-one

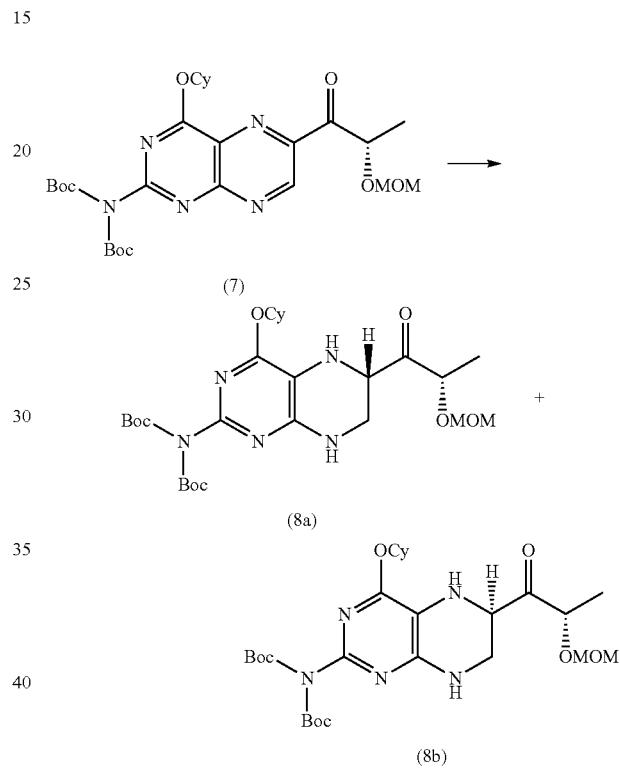

The procedure of Example 29 was repeated, except that 1-[4-cyclohexyloxy-2-(N,N-di-tert-butoxycarbonyl)aminopteridin-6-yl]-2 S-methoxymethoxypropan-1-one (200 mg, 0.36 mmol) was used, to thereby yield 1-[4-cyclohexyloxy-2-(N,N-di-tert-butoxycarbonyl)amino-5,6,7,8-tetrahydropteridin-6-yl]-2S-methoxymethoxypropan-1-one (76 mg, 0.13 mmol, yield: 38%).

$^1$H NMR (DMSO-d$^6$): δ/ppm=1.21 (d, 3H, J=6.9 Hz), 1.32-1.37 (m, 3H), 1.38 (s, 18H), 1.43-1.51 (m, 3H), 1.73 (m, 2H), 1.89-1.91 (m, 2H), 3.27 (s, 3H), 3.51-3.56 (m, 2H), 4.33-4.35 (m, 1H), 4.41 (q, 1H, J=6.9 Hz), 4.59 (d, 1H, J=6.9 Hz), 4.67 (d, 1H, J=6.9 Hz), 4.86-4.89 (m, 1H), 4.95 (d, 1H, J=2.7 Hz), 7.08 (s, 1H)

$^1$H NMR (DMSO-d$^6$): δ/ppm=1.24 (d, 3H, J=6.9 Hz), 1.32-1.37 (m, 3H), 1.38 (s, 18H), 1.43-1.51 (m, 3H), 1.73 (m, 2H), 1.89-1.91 (m, 2H), 3.32 (s, 3H), 3.51-3.56 (m, 2H), 4.33-4.35 (m, 1H), 4.39 (q, 1H, J=6.9 Hz), 4.59 (d, 1H, J=6.9 Hz), 4.67 (d, 1H, J=6.9 Hz), 4.86-4.89 (m, 1H), 5.01 (d, 1H, J=2.4 Hz), 7.08 (s, 1H)

Example 33

Synthesis of 2-amino-6-(2S-hydroxypropionyl)-7,8-dihydro-3H-pteridin-4-one (S-sepiapterin))

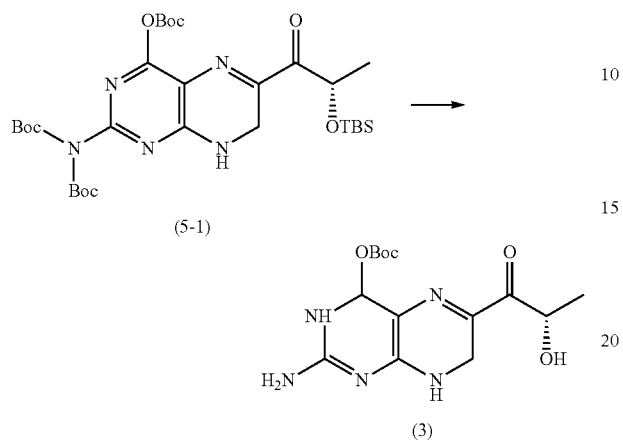

Acetonitrile (3 mL) and 2 mol/L hydrochloric acid (6 mL) were added to 1-[4-tert-butoxycarbonyl-2-(N,N-di-tert-butoxycarbonyl)amino-7,8-dihydropteridin-6-yl]-2 S-tert-butyldimethylsilanyloxypropan-1-one (300 mg, 0.46 mmol), and the mixture was stirred at an external temperature of 40° C. for 3 hours. The pH of the reaction mixture was adjusted with aqueous sodium hydroxide solution to 7. The formed crystals were recovered through filtration and dried under reduced pressure, to thereby yield S-sepiapterin (96 mg, 0.40 mmol, yield: 88%). The thus-produced compound was found to have the same spectral data as those obtained in Example 4.

Example 34

Synthesis of 2-amino-6R-(2S-hydroxypropionyl)-5,6,7,8-tetrahydro-3H-pteridin-4-one (6R—S-tetrahydrolactoylpterin) dihydrochloride

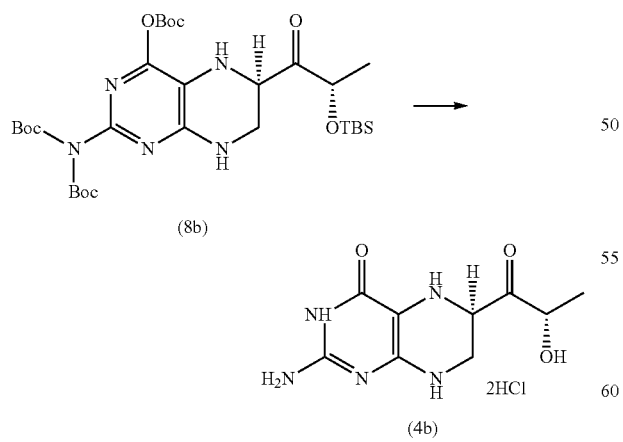

Concentrated hydrochloric acid (10 mL) was added to 1-[4-tert-butoxycarbonyl-2-(N,N-di-tert-butoxycarbonyl) amino-5,6,7,8-tetrahydropteridin-6R-yl]-2S-tert-butyldimethylsilanyloxypropan-1-one (8b) (393 mg, 0.60 mmol), and the mixture was concentrated under reduced pressure. Ethanol was added to the concentrate. The formed crystals were recovered through filtration and dried under reduced pressure, to thereby yield 6R—S-tetrahydrolactoylpterin dihydrochloride (4b) (106 mg, 0.34 mmol, yield: 56%). The thus-produced compound was found to have the same spectral data as those obtained in Example 8.

The invention claimed is:
1. A method for producing sepiapterin represented by formula (3):

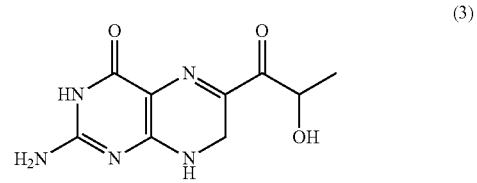 [SMILES: CC(O)C(=O)C1=Nc2c(nc(N)[nH]c2=O)NC1]

or a salt thereof, the method comprising:
subjecting lactoylpterin represented by formula (2):

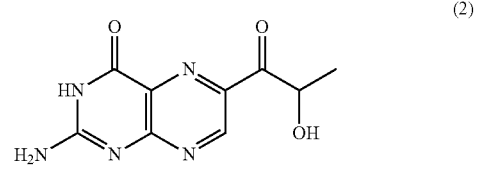 [SMILES: CC(O)C(=O)c1cnc2nc(N)[nH]c(=O)c2n1]

or a salt thereof to reduction by use of a sulfite, a hyposulfite or a thiosulfate, or catalytic reduction under basic conditions.

2. A method for producing sepiapterin represented by formula (3):

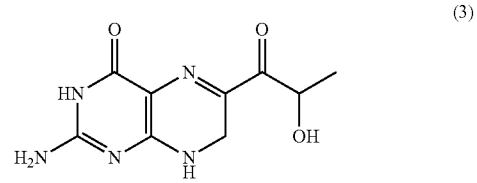 [SMILES: CC(O)C(=O)C1=Nc2c(nc(N)[nH]c2=O)NC1]

or a salt thereof, the method comprising:
subjecting tetrahydrolactoylpterin represented by formula (4):

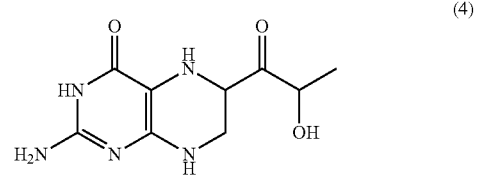 [SMILES: CC(O)C(=O)C1CNc2nc(N)[nH]c(=O)c2N1]

or a salt thereof to oxidation by use of a peracid, or air oxidation under neutral or basic conditions.

3. A method for producing tetrahydrolactoylpterin represented by formula (4):

or a salt thereof, the method comprising:
subjecting lactoylpterin represented by formula (2):

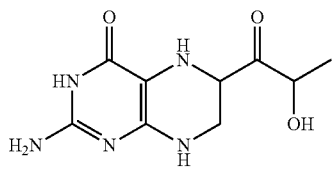
(4)

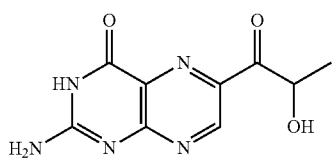
(2)

or a salt thereof to reduction by use of a BH$_3$-based reducing agent, or catalytic reduction under basic conditions.

4. The method according to claim 3, wherein the reduction reaction is reduction by use of a BH$_3$-based reducing agent under acidic conditions, or catalytic reduction under basic conditions.

5. A method for producing sepiapterin represented by formula (3):

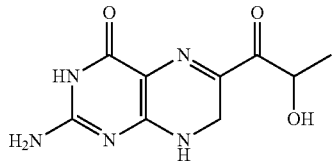
(3)

or a salt thereof, the method comprising:
subjecting lactoylpterin represented by formula (2):

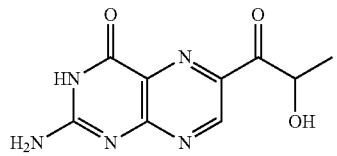
(2)

or a salt thereof to reduction by use of a BH$_3$-based reducing agent, or catalytic reduction under basic conditions, to thereby form tetrahydrolactoylpterin represented by formula (4):

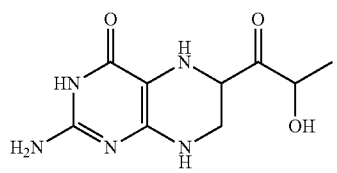
(4)

or a salt thereof, and
subsequently subjecting the compound (4) to oxidation by use of a peracid, or air oxidation under neutral or basic conditions.

6. The method according to claim 5, wherein the reduction reaction is reduction by use of a BH$_3$-based reducing agent under acidic conditions, or catalytic reduction under basic conditions.

* * * * *